US011078148B2

(12) United States Patent
Cronin et al.

(10) Patent No.: US 11,078,148 B2
(45) Date of Patent: Aug. 3, 2021

(54) METHODS FOR THE REDUCTION OF CARBON DIOXIDE

(71) Applicant: UNIVERSITY OF LOUISVILLE RESEARCH FOUNDATION, INC., Louisville, KY (US)

(72) Inventors: Steve P. Cronin, Louisville, KY (US); Craig A. Grapperhaus, Jeffersonville, IN (US); Robert M. Buchanan, Louisville, KY (US); Jacob M. Strain, Louisville, KY (US); Joshua M. Spurgeon, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 0 days.

(21) Appl. No.: 16/803,027

(22) Filed: Feb. 27, 2020

(65) Prior Publication Data

US 2020/0277248 A1 Sep. 3, 2020

Related U.S. Application Data

(60) Provisional application No. 62/811,746, filed on Feb. 28, 2019.

(51) Int. Cl.
| | |
|---|---|
| *C07C 51/41* | (2006.01) |
| *B01J 31/18* | (2006.01) |
| *C25B 3/04* | (2006.01) |
| *C25B 11/04* | (2021.01) |
| *C25B 11/12* | (2006.01) |
| *C07C 53/06* | (2006.01) |
| *C25B 3/25* | (2021.01) |
| *C25B 11/043* | (2021.01) |
| *C25B 11/057* | (2021.01) |

(52) U.S. Cl.
CPC .............. *C07C 51/41* (2013.01); *B01J 31/181* (2013.01); *C25B 3/25* (2021.01); *B01J 2531/0238* (2013.01); *B01J 2531/26* (2013.01); *C07C 53/06* (2013.01); *C25B 11/043* (2021.01); *C25B 11/057* (2021.01)

(58) Field of Classification Search
CPC C07C 51/41; C07C 53/26; C25B 3/04; C25B 11/0415; C25B 11/12
USPC ....................................................... 562/512
See application file for complete search history.

(56) References Cited

FOREIGN PATENT DOCUMENTS

WO   WO-2005030686 A1 *  4/2005  ......... C07C 29/1514

OTHER PUBLICATIONS

Khusnutdinova et al. (2015) "Metal—Ligand Cooperation" Angew. Chem. Int. Ed., vol. 54, pp. 12236-12273.
Kondratenko et al. (2013) "Status and perspectives of CO2 conversion into fuels and chemicals by catalytic, Dhotocatalytic and electrocatalytic processes" Energy Environ. Sci., vol. 6, pp. 3112-3135.
Komienko et al. (2015) "Metal—Organic Frameworks for Electrocatalytic Reduction of Carbon Dioxide" J. Am. Chem. Soc., vol. 137, pp. 14129-14135.
Kumagai et al. (2019) "Electrocatalytic reduction of low concentration CO2" Chem. Sci., vol. 10, pp. 1597-1606.
Kumar et al. (2014) "Kinetic Effects of Sulfur Oxidation on Catalytic Nitrile Hydration: Nitrile Hydratase Insights from Bioinspired Ruthenium(II) Complexes" Inorg. Chem., vol. 53, pp. 12372-12377.
Kumar et al. (2016) "Controlling the Product Syngas H2:CO Ratio through Pulsed-Bias Electrochemical Reduction of CO2 on Copper" ACS Catal., vol. 6, pp. 4739-4745.
Kumar et al. (2016) "New trends in the development of heterogeneous catalysts for electrochemical CO2 reduction" Catal Today, vol. 270, pp. 19-30.
Kumar et al. (2017) "Reduced SnO2 Porous Nanowires with a High Density of Grain Boundaries as Catalysts for Efficient Electrochemical CO2-into-HCOOH Conversion" Angew. Chem. Int. Ed., vol. 56, pp. 3645-3649.
Kumari et al. (2016) "Solar Hydrogen Production from Seawater Vapor Electrolysis" Energy Environ. Sci., vol. 9, pp. 1725-1733.
Kumari et al. (2017) "A low-noble-metal W1-x1rxO3-E water oxidation electrocatalyst for acidic media via rapid plasma synthesis" Energy Environ. Sci., vol. 10, pp. 2432-2440.
Kütt et al. (2006) "A Comprehensive Self-Consistent Spectrophotometric Acidity Scale of Neutral Bronsted Acids in Acetonitrile" J. Org. Chem., vol. 71, pp. 2829-2838.
Last et al. (2015) "A review of major non-power-related carbon dioxide stream compositions." Environ. Earth Sci., vol. 14, pp. 1189-1198.
Lee et al. (2017) "Electrochemical and spectroscopic methods for evaluating molecular electrocatalysts" Nat. Rev. Chem., vol. 1, Article 0039 (14 pages).
Leung et al. (2014) "An overview of current status of carbon dioxide capture and storage technologies" Renew. Sust. Energ. Rev., vol. 39, pp. 426-443.
Lichterman et al. (2013) "Enhanced Stability and Activity for Water Oxidation in Alkaline Media with Bismuth Vanadate Photoelectrodes Modified with a Cobalt Oxide Catalytic Layer Produced by Atomic Layer Deposition" J. Phys. Chem. Lett., vol. 4, pp. 4188-4191.
Liu et al.(2014) "Enhanced photoelectrochemical water-splitting performance of semiconductors by surface Dassivation layers" Energy Environ. Sci., vol. 7, pp. 2504-2517.

(Continued)

*Primary Examiner* — Deborah D Carr
(74) *Attorney, Agent, or Firm* — ALGM LLP; Harry J. Guttman

(57) ABSTRACT

Some embodiments of the invention include methods of using a compound (e.g., Formula (I)) for the reduction of carbon dioxide to formate by contacting the carbon dioxide with a composition comprising a compound. In certain embodiments, the source of the carbon dioxide is air or is flue gas. Additional embodiments of the invention are also discussed herein.

28 Claims, 6 Drawing Sheets

(5 of 6 Drawing Sheet(s) Filed in Color)

(56) References Cited

OTHER PUBLICATIONS

Liu et al. (2016) "Enhanced electrocatalytic CO2 reduction via field-induced reagent concentration" Nature, vol. 537, pp. 382-386.

Lu et al. (2014) "Synthesis, Crystal Structure, and Biological Activity of an Mn(II) Complex Derived from 2,6-diacetylpyridine bis(N. 4-methylthiosemicarbazone)" Synth. React. Inorg., Mel-Org., Nano-Met. Chem., vol. 44, pp. 1068-1072.

Lu et al. (2018) "Efficient electrocatalytic reduction of CO2 to CO on an electrodeposited Zn porous network" Electrochem. Commun., vol. 97, pp. 87-90.

Mandal et al. (1993) "Reaction of electrophiles with manganese(I) and rhenium(I) alkoxide complexes: reversible absorption of atmospheric carbon dioxide" Organometallics, vol. 12, pp. 1714-1719.

Mayer et al. (1975) "The acceptor Number—A quantitative empirical parameter for the electrophilic properties of solvents" Monatsh. Chem., vol. 106, pp. 1235-1257.

McDowell et al. (2014) "Improved Stability of Polycrystalline Bismuth Vanadate Photoanodes by Use of Dual-Layer Thin TiO2/Ni Coatings" J. Phys. Chem. C, vol. 118, pp. 19618-19624.

Miguel et al. (2014) "Theoretical Prediction of pKa in Methanol: Testing SM8 and SMD Models for Carboxylic Acids, Phenols, and Amines" J. Phys. Chem. B, vol. 118, pp. 5730-5739.

Morimoto et al. (2013) "CO2 Capture by a Rhenium(I) Complex with the Aid of Triethanolamine" J. Am. Chem. Soc., vol. 135, pp. 16825-16828.

Mota et al. (2019) "From CO2 methanation to ambitious long-chain hydrocarbons: alternative fuels paving the path to sustainability" Chem. Soc. Rev., vol. 48, pp. 205-259.

Ngo et al. (2017) "Turning on the Protonation-First Pathway for Electrocatalytic CO2 Reduction by Manganese Bipyridyl Tricarbonyl Complexes" J. Am. Chem. Soc., vol. 139, pp. 2604-2618.

Nichols et al. (2018) Electrocatalytic Reduction of CO2 to Formate by an Iron Schiff Base Complex Inorg. Chem., vol. 37, pp. 2111-2121.

Ouch et al. (2011) "Metal-Stabilized Thiyl Radicals as Scaffolds for Reversible Alkene Addition via C—S Bond Formation/Cleavage" Inorg. Chem., vol. 50, pp. 9904-9914.

Pedrido et al. (2005) "Syntheses and X-ray characterization of metal complexes with the pentadentate .hiosemicarbazone ligand bis(4-N-methylthiosemicarbazone)-2,6-diacetylpyridine. The first pentacoordinate lead(II) complex with a pentagonal geometry" Dalton Trans. vol. 2005, No. 3, pp. 572-579.

Pedrido et al. (2008) "Pentadentate thiosemicarbazones as versatile chelating systems. A comparative structural study of their metallic complexes" Dalton Trans. vol. 2008, No. 47, pp. 6776-6787.

Qiao et al. (2014) "A review of catalysts for the electroreduction of carbon dioxide to produce low-carbon fuels" Chem. Soc. Rev., vol. 43, pp. 631-675.

Raciti et al. (2018) "Recent Advances in CO2 Reduction Electrocatalysis on Copper" ACS Energy Lett., vol. 3, pp. 1545-1556.

Rao et al. (2018) "Photoelectrochemical reduction of CO2 to HCOOH on silicon photocathodes with reduced SnO2 borous nanowire catalysts" J. Mater Chem. A, vol. 6, pp. 1736-1742.

Rauch et al. (2017) "Zinc and Magnesium Catalysts for the Hydrosilylation of Carbon Dioxide" J. Am. Chem. Soc., vol. 139, pp. 18162-18165.

Roubelakis et al. (2012) "Proton-coupled electron transfer kinetics for the hydrogen evolution reaction of hangman porphyrins" Energy Environ. Sci., vol. 5, pp. 7737-7740.

Rountree et al. (2014) "Evaluation of Homogeneous Electrocatalysts by Cyclic Voltammetry" Inorganic Chemistry, vol. 53, No. 19, pp. 9983-10002.

Roy et al. (2017) "Molecular Cobalt Complexes with Pendant Amines for Selective Electrocatalytic Reduction of carbon Dioxide to Formic Acid" Journal of the American Chemical Society, vol. 139, No. 10, pp. 3685-3696.

Sampson et al. (2014) "Manganese Catalysts with Bulky Bipyridine Ligands for the Electrocatalytic Reduction of carbon Dioxide: Eliminating Dimerization and Altering Catalysis" J. Am. Chem. Soc., vol. 136, pp. 5460-5471.

Saouma et al. (2012) "Protonation and Concerted Proton—Electron Transfer Reactivity of a Bis-Benzimidazolate Ligated [2Fe-2S1] Model for Rieske Clusters" J. Am. Chem. Soc., vol. 134, pp. 7293-7296.

Saraei et al. (2018) "Streams, cascades, and pools: various water cluster motifs in structurally similar Ni(II) complexes" CrystEngComm, vol. 20, pp. 7071-7081.

Saraei et al. (2019) "Water wire clusters in isostructural Cu(II) and Ni(Ii) complexes: Synthesis, characterization, and termal analyses" Inorg. Chim. Acta, vol. 492, pp. 268-274.

Schouten et al. (2011) "A new mechanism for the selectivity to C1 and C2 species in the electrochemical reduction of aarbon dioxide on copper electrodes" Chem. Sci., vol. 2, pp. 1902-1909.

Sgro et al. (2012) "Frustrated Lewis Pair Inspired Carbon Dioxide Reduction by a Ruthenium Tris(aminophosphine) complex" Angew. Chem. Int. Ed., vol. 51, pp. 11343-11345.

Sheldrick (2008) "A short history of SHELX" Acta Crystallogr, vol. A64, pp. 112-122.

Spurgeon et al. (2011) "Proton exchange membrane electrolysis sustained by water vapor" Energy Environ. Sci., vol. 4, pp. 2993-2998.

Spurgeon et al. (2014) "Improving O2 Production of WO3 Photoanodes with Ir02 in Acidic Aqueous Electrolyte" PCCP, vol. 16, pp. 3623-3631.

Spurgeon et al. (2018) "A comparative technoeconomic analysis of pathways for commercial electrochemical CO2 reduction to liquid products" Energy Environ. Sci., vol. 11, pp. 1536-1551.

Stephan et al. (2014) "Frustrated Lewis pair chemistry of carbon, nitrogen and sulfur oxides" Chem. Sci., vol. 5, pp. 2625-2641.

Stephan (2016) "The broadening reach of frustrated Lewis pair chemistry" Science, vol. 354, No. 6317, Article aaf7229 (10 pages).

Straistari et al. (2017) "A Thiosemicarbazone—Nickel(II) Complex as Efficient Electrocatalyst for Hydrogen Evolution" ChemCatChem, vol. 9, pp. 2262-2268.

Straistari et al. (2018) "Hydrogen Evolution Reactions Catalyzed by a Bis(thiosemicarbazone) Cobalt Complex: An Experimental and Theoretical Study" Chem. -Eur. J., vol. 24, pp. 8779-8786.

Straistari et al. (2018) "Influence of the Metal Ion on the Electrocatalytic Hydrogen Production by a Thiosemicarbazone Palladium Complex" Fur. J. Inorg. Chem., vol. 2018, No. 20-21, pp. 2259-2266.

Taheri et al. (2015) "An Iron Electrocatalyst for Selective Reduction of CO2 to Formate in Water: Including Thermochemical Insights" ACS Catalysis, vol. 5, pp. 7140-7151.

Theaker et al. (2018) "Heterogeneously catalyzed two-step cascade electrochemical reduction of CO2 to ethanol" Electrochim. Acta, vol. 274, pp. 1-8.

Toma et al. (2016) "Mechanistic insights into chemical and photochemical transformations of bismuth vanadate photoanodes" Nat. Commun. vol. 7, Article 12012 (11 pages).

Trickett et al. (2017) "The chemistry of metal—organic frameworks for CO2 capture, regeneration and conversion" Nature Reviews Materials, vol. 2, Article 17045 (16 pages).

Trott et al. (2016) "Catalysts for CO2/epoxide ring-opening copolymerization" Philos. Trans. Royal Soc. A, vol. 374, No. 2061, Article 20150085 (19 pages).

Un General Assembly (2015) "Transforming our world: the 2030 Agenda for Sustainable Development; A/RES/70/1" available at: https://www.refworld.org/docid/57b6e3e44.html (35 pages).

Venkatachalam et al. (2018) "A Novel Strategy to Introduce 18F, a Positron Emitting Radionuclide, into a Gallium Nitrate Complex: Synthesis, NMR, X-Ray Crystal Structure, and Preliminary Studies on Radiolabelling with 18F" Aust. J. Chem., vol. 71, pp. 81-86.

Vickers et al. (2017) "Electrochemical Carbon Dioxide Reduction at Nanostructured Gold, Copper, and Alloy Materials" Energy Technol., vol. 5, pp. 775-795.

Voosen (2019) "New climate models forecast a warming surge" Science, vol. 364, No. 6437, pp. 222-223.

Walczak et al. (2015) "Modeling, Simulation, and Fabrication of a Fully Integrated, Acid-stable, Scalable Solar-Driven Water-Splitting System" ChemSusChem, vol. 8, pp. 544-551.

Waldie et al. (2018) "Hydricity of Transition-Metal Hydrides: Thermodynamic Considerations for CO2 Reduction" ACS Catal., vol. 8, pp. 1313-1324.

(56) References Cited

OTHER PUBLICATIONS

White et al. (2017) "Simulations of non-monolithic tandem solar cell configurations for electrolytic fuel generation" J. Mater. Chem. A, vol. 5, pp. 13112-13121.

Wiedner et al. (2016) "Thermodynamic Hydricity of Transition Metal Hydrides" Chem. Rev., vol. 116, pp. 8655-8692.

Wilson et al. (2006) "Hydrogen Oxidation and Production Using Nickel-Based Molecular Catalysts with Positioned Proton Relays" Journal of the American Chemical Society, vol. 128 No. 1, pp. 358-366.

Wu et al. (2016) "Catalytic conversion of CO2 to value added fuels: Current status, challenges, and future directions" Chin. J. Catal., vol. 37, pp. 999-1015.

Wuttig et al. (2017) "Bicarbonate Is Not a General Acid in Au-Catalyzed CO2 Electroreduction" J. Am. Chem. Soc., vol. 139, pp. 17109-17113.

Xia et al. (2019) "Continuous production of pure liquid fuel solutions via electrocatalytic CO2 reduction using solid-electrolyte devices" Nature Energy, vol. 4, pp. 776-785.

Yang et al. (2017) "CO2 Conversion to Formic Acid in a Three Compartment Cell with Sustainionm Membranes" ECS Transactions, vol. 77, pp. 1425-1431.

Zhang et al. (2016) "Reversible methanol addition to copper Schiff base complexes: a kinetic, structural and spectroscopic study of reactions at azomethine C=N bonds" Dalton Trans., vol. 45, pp. 15791-15799.

Zhang et al. (2017) "Translation of Ligand-Centered Hydrogen Evolution Reaction Activity and Mechanism of a Rhenium-Thiolate from Solution to Modified Electrodes: A Combined Experimental and Density Functional Theory Study" Inorg. Chem., vol. 56, pp. 2177-2187.

Zhang et al. (2019) "Interplay of Homogeneous Reactions, Mass Transport, and Kinetics in Determining Selectivity of the Reduction of CO2 on Gold Electrodes" ACS Cent. Sci., vol. 5, pp. 1097-1105.

Zhao et al. (2015) "Properties of carbon dioxide absorption and reduction by sodium borohydride under atmospheric pressure" Fuel, vol. 142, pp. 1-8.

Zhao et al. (2017) "Progress in catalyst exploration for heterogeneous CO2 reduction and utilization: a critical review" J. Mater. Chem. A, vol. 5, pp. 21625-21649.

Zhou et al. (2018) "Dopant-induced electron localization drives CO2 reduction to C2 hydrocarbons" Nat. Chem., vol. 10, pp. 974-980.

Aghaie et al. (2018) "A systematic review on CO2 capture with ionic liquids: Current status and future prospects" Renew. Sust. Energ. Rev., vol. 96, pp. 502-525.

Ajayi et al. (2016) "A rapid and scalable methode for making mixed metal oxide solid solution for enabling accelerated materials discovery" J. Mater. Res. vol. 31, No. 11, pp. 1596-1607.

An et al. (2009) "Synthesis, Structure, Assembly, and Modulation of the CO2 Adsorption Properties of a Zinc-Adeninate Macrocycle" JACS, vol.131, No. 24, pp. 8401-8403.

Appel et al. (2013) "Frontiers, Opportunities, and Challenges in Biochemical and Chemical Catalysis of CO2 Fixation" Chem Rev., vol. 113, pp. 6621-6658.

Arakawa et al. (2001) "Catalysis Research of Relevance to Carbon Management: Progress, Challenges, and Opportunities" Chem. Rev., vol. 101, pp. 953-996.

Arikawa et al. (2015) "Fixation of atmospheric carbon dioxide by ruthenium complexes bearing an NHC-based pincer ligand: formation of a methylcarbonato complex and its methylation." Dalton Trans., vol. 44, pp. 5303-5305.

Arrowsmith et al. (2011) "Fluorescent gallium and indium bis(thiosemicarbazonates) and their radiolabelled analogues: Synthesis, structures and cellular confocal fluorescence imaging investigations" Dalton Trans., vol. 40, pp. 6238-6252.

Ashley et al. (2009) "Non-Metal-Mediated Homogeneous Hydrogenation of CO2 to CH3OH" Angew. Chem. Int. Ed., vol. 48, pp. 9839-9843.

Banerjee et al. (2008) "High-Throughput Synthesis of Zeolitic Imidazolate Frameworks and Application to CO2 Capture" Science, vol. 319, No. 5865, pp. 939-943.

Barton Cole et al. (2010) "Using a One-Electron Shuttle for the Multielectron Reduction of CO2 to Methanol: Kinetic, Mechanistic, and Structural Insights" J. Am. Chem. Soc., vol. 132, pp. 11539-11551.

Beckett et al. (1996) "A convenient N.M.R. method for the measurement of Lewis acidity at boron centres: correlation of reaction rates of Lewis acid initiated epoxide polymerizations with Lewis acidity" Polymer, vol. 37, pp. 4629-4631.

Bewick et al. (1969) "The electroreduction of CO2 to malate on a mercury cathode" Tetrahedron Lett., vol. 10, pp. 4623-4626.

Birhanu et al. (2018) "Copper and Copper-Based Bimetallic Catalysts for Carbon Dioxide Electroreduction" Adv. Mater. Interfaces, vol. 2018, Article 1800919 (34 pages).

Brown et al. (2017) "Copper complexes with dissymmetrically substituted bis(thiosemicarbazone) ligands as a basis for PET radiopharmaceuticals: control of redox potential and lipophilicity" Dalton Trans., vol. 46, pp. 14612-14630.

Calatayud et al. (2012) "Complexes of group 12 metals containing a hybrid thiosemicarbazone-pyridylhydrazone igand" Inorganica Chimica Acta, vol. 381, pp. 150-161.

Calvary et al. (2019) "Synthesis, Characterization, and HER Activity of Pendant Diamine Derivatives of NiATSM" Eur. J. Inorg. Chem., vol. 2019, No. 33, pp. 3782-3790.

Cheng et al. (2001) "Single-Site β-Diiminate Zinc Catalysts for the Alternating Copolymerization of CO2 and Epoxides: Catalyst Synthesis and Unprecedented Polymerization Activity" J. Am. Chem. Soc., vol.123, pp. 8738-8749.

Costentin et al. (2013) "Electrochemistry of Acids on Platinum. Application to the Reduction of Carbon Dioxide in the Presence of Pyridinium Ion in Water" J. Am. Chem. Soc., vol. 135, pp. 17671-17674.

Cowley et al. (2006) "Copper Complexes of Thiosemicarbazone-Pyridylhydrazine (Thynic) Hybrid Ligands: A New Versatile Potential Bifunctional Chelator for Copper Radiopharmaceuticals" Inorganic Chemistry, vol. 45, No. 2, pp. 496-498.

Cronin et al. (2019) "Utilizing Charge Effects and Minimizing Intramolecular Proton Rearrangement to Improve the Overpotential of a Thiosemicarbazonato Zinc Her Catalyst" Inorganic Chemistry, vol. 58, No 19, pp 12986-12997.

Cronin et al. (2020) "Exploiting Metal-Ligand Cooperativity to Sequester, Activate, and Reduce Atmospheric Carbon Dioxide with a Neutral Zinc Complex" Inorganic Chemistry, vol. 59, No. 7, pp. 4835-4841.

Davis, Anna E, "Facile and efficient synthesis of thiosemicarbazone derivatives with functionalized pendant amines." (2019). ThinkIR: The University of Louisville's Institutional Repository, College of Arts & Sciences Senior Honors Theses. Paper 202. (35 pages).

Ding et al. (2019) "Carbon capture and conversion using metal—organic frameworks and MOF-based materials" Chem. Soc. Rev., vol. 48, pp. 2783-2828.

Dobrovetsky et al. (2013) "Catalytic Reduction of CO2 to CO by Using Zinc(II) and in Situ Generated Carbodiphosphoranes" Angew. Chem. Int. Ed., vol. 52, pp. 2516-2519.

Dutcher et al. (2015) "Amine-Based CO2 Capture Technology Development from the Beginning of 2013—A Review" ACS Appl. Mater. Interfaces, vol. 7, pp. 2137-2148.

Eggins et al. (1993) "Photoreduction of carbon dioxide on zinc sulfide to give four-carbon and two-carbon acids" J. Chem. Soc., Chem. Commun., vol. 1993, No. 4, pp 349-350.

Farrugia (1997) "ORTEP-3 for Windows a version of ORTEP-III with a Graphical User Interface (GUI)" J. Appl. Crystallogr. vol. 30, p. 565.

Finlay et al. (2013) "Triazolo and imidazo dihydropyrazolopyrimidine potassium channel antagonists" Bioorg. Med. Chem. Lett., vol. 23, pp. 1743-1747.

Fogg et al. Carbon Dioxde in Non-aqueous Solvents at Pressures Less Than 200 KPa; Oxford; New York, 1992.

Fourmond et al. (2010) "H2 Evolution and Molecular Electrocatalysts: Determination of Overpotentials and Effect of Homoconjugation" Inorganic Chemistry, vol. 49, No. 22, pp. 10338-10347.

(56) References Cited

OTHER PUBLICATIONS

Francke et al. (2018) "Homogeneously Catalyzed Electroreduction of Carbon Dioxide—Methods, Mechanisms, and Catalysts" Chem. Rev., vol. 118, pp. 4631-4701.

Franco et al. (2017) "Local Proton Source in Electrocatalytic CO2 Reduction with [Mn(bpy—R)(CO)3Br] Complexes" Chemistry—A European Journal, vol. 23, pp. 4782-4793.

Grills et al. (2014) "Electrocatalytic CO2 Reduction with a Homogeneous Catalyst in Ionic Liquid: High Catalytic Activity at Low Overpotential" The Journal of Physical Chemistry Letters, vol. 5, No. 11, pp. 2033-2038.

Gulati et al. (2019) "Photocatalytic hydrogen evolution on Si photocathodes modified with bis(thiosemicarbazonato) nickel(II)/Nafion" Chem. Commun., vol. 55, pp. 9440-9443.

Gupta et al. (2019) "Effect of Stacking Interactions on the Translation of Structurally Related Bis(thiosemicarbazonato) nickel(II) HER Catalysts to Modified Electrode Surfaces" Inorg. Chem., vol. 58, pp. 12025-12039.

Guterres, A. The Sustainable Development Goals Report; New York, New York, 2018. (40 pages).

Haddad et al. (2015) "Proposed Ligand-Centered Electrocatalytic Hydrogen Evolution and Hydrogen Oxidation at a Noninnocent Mononuclear Metal—Thiolate" J. Am. Chem. Soc., vol. 137, pp. 9238-9241.

Haddad et al. (2016) "Beyond Metal-Hydrides: Non-Transition-Metal and Metal-Free Ligand-Centered Electrocatalytic Hydrogen Evolution and Hydrogen Oxidation" J. Am. Chem. Soc., vol. 138, pp. 7844-7847.

Haddad et al. (2017) "Metal-Assisted Ligand-Centered Electrocatalytic Hydrogen Evolution upon Reduction of a Bis (thiosemicarbazonato)Cu(II) Complex" Inorganic Chemistry, vol. 56, No. 18, pp. 11254-11265.

Hao et al. (2011) "Structurally Designed Synthesis of Mechanically Stable Poly(benzoxazine-co-resol)-Based Porous Carbon Monoliths and Their Application as High-Performance CO2 Capture Sorbents" JACS, vol. 133, No. 29, pp. 11378-11388.

Haussener et al. (2012) "Modeling, simulation, and design criteria for photoelectrochemical water-splitting systems" Energy Environ. Sci., vol. 5, pp. 9922-9935.

Holland et al. (2007) "Functionalized Bis(thiosemicarbazonato) Complexes of Zinc and Copper: Synthetic Platforms Toward Site-Specific Radiopharmaceuticals" Inorg. Chem., vol. 46, pp. 465-485.

Jain et al. (2018) "Ligand-Assisted Metal-Centered Electrocatalytic Hydrogen Evolution upon Reduction of a Bis (thiosemicarbazonato)Ni(II) Complex" Inorg. Chem., vol. 57, pp. 13486-13493.

Jiang et al. (2019) "A look at periodic trends in d-block molecular electrocatalysts for CO2 reduction" Dalton Trans., vol. 48, pp. 9454-9468.

Kaljurand et al. (2005) "Extension of the Self-Consistent Spectrophotometric Basicity Scale in Acetonitrile to a Full Span of 28 pKa Units: Unification of Different Basicity Scales" J. Org. Chem., vol. 70, pp. 1019-1028.

Kato et al. (1985) "Facile carbon dioxide uptake by zinc(II)-tetraazacycloalkane complexes. 1. Syntheses, Characterizations, and chemical properties of (monoalkyl carbonato)(tetraazacycloalkane)zinc(II) complexes" Inorg. Chem., vol. 24, pp. 504-508.

Kato et al. (1985) "Facile carbon dioxide uptake by zinc(II)-tetraazacycloalkane complexes. 2. X-ray structural studies of (μ-monomethyl carbonato)[(1,4,8,11-tetraazacyclotetradecane)zinc(II)] perchlorate, bis(μ-monomethyl carbonato)tris (1,4,8,12-tetraazacyclopentadecane)zinc(I) perchlorate, and (monomethyl carbonato)(1,4,8,11-tetramethyl-1,4,8,11-tetraazacyclotetradecane)zinc(II) perchlorate" Inorg. Chem., vol. 24, pp. 509-514.

Keith et al. (2018) "A Process for Capturing CO2 from the Atmosphere" Joule, vol. 2, pp. 1573-1594.

\* cited by examiner

METHODS FOR THE REDUCTION OF CARBON DIOXIDE

CROSS-REFERENCE TO RELATED APPLICATIONS

This application claims the benefit of U.S. Provisional Application No. 62/811,746, filed Feb. 28, 2019 entitled "Methods and Compositions for the Homogenous Reduction of Atmospheric Carbon Dioxide" which is herein incorporated by reference in its entirety.

GOVERNMENT RIGHTS

This invention was made with government support under CHE-1665136 and CHE-1800245 both awarded by the National Science Foundation. The government has certain rights in the invention.

BACKGROUND

Although the degree of its effects remains in debate, the current atmospheric concentration of carbon dioxide ($CO_2$) is in excess of 415 ppm creating impacts on climate, global temperatures, and ocean acidification. Goal 13 of The 2030 Agenda for Sustainable Development by the United Nations identifies the need to "take urgent action to combat climate change and its impacts." The 2018 U. N. report calls for "urgent and accelerated action" as the five-year global temperature from 2013-2017 is the highest on record. Balancing the carbon cycle by sequestering $CO_2$ and/or utilizing it as a feedstock for liquid fuels provides one of several approaches to address $CO_2$ levels. Currently, the initial steps of this process appear to require one method to capture low concentrations of $CO_2$ from the atmosphere or flue gas and a second system to reduce $CO_2$ to value added products.

Certain embodiments of the invention address one or more of the deficiencies described above. Some embodiments of the invention include methods of using a compound (e.g., Formula (I)) for the reduction of carbon dioxide to formate by contacting the carbon dioxide with a composition comprising a compound. In certain embodiments, the source of the carbon dioxide is air or is flue gas. Additional embodiments of the invention are also discussed herein.

SUMMARY

Some embodiments of the present invention include a method for producing formate from carbon dioxide comprising contacting carbon dioxide with a composition, where the composition comprises (a) a compound selected from Formula (I), salts, optical isomers, geometric isomers, salts of isomers, derivatives thereof, and solvent associated complexes thereof, (b) a solution solvent, and (c) an acid. In other embodiments, Formula (I) is

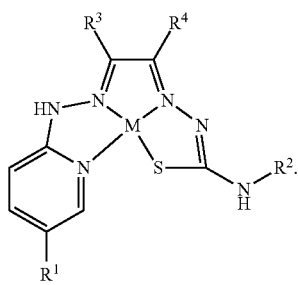

(I)

In still other embodiments, $R^1$ is monovalent H, halogen, —CN, nitro (—$NO_2$), —$NH_2$, —$N(CH_3)_2$, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which —$NH_2$, —$N(CH_3)_2$, methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy. In yet other embodiments, $R^2$ can be monovalent H, halogen, —CN, nitro (—$NO_2$), —$NH_2$, —$N(CH_3)_2$, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which —$NH_2$, —$N(CH_3)_2$, methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy. In certain embodiments, $R^3$ can be monovalent H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluoronated alkyl, —$CF_3$, —$OCF_3$, or $C_1$-$C_3$ alkoxy. In some embodiments, $R^4$ can be monovalent H, halogen, —CN, hydroxy (—OH), methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl, which methanoyl (—COH), carboxy (—$CO_2H$), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluorinated alkyl, —$CF_3$, —$OCF_3$, or $C_1$-$C_3$ alkoxy. In other embodiments, $R^3$ and $R^4$ are optionally bonded together to form a ring, where the ring that is formed can be cycloalkyl, heterocyclyl, aryl, or heteroaryl, which cycloalkyl, heterocyclyl, aryl, or heteroaryl can optionally be substituted with one or more of halogen, oxo (=O), hydroxy (—OH), methanoyl (—COH), carboxy (—$CO_2H$), nitro (—$NO_2$), —$NH_2$, —$N(CH_3)_2$, cyano (—CN), ethynyl (—CCH), propynyl, sulfo (—$SO_3H$), morpholinyl, —CO-morpholin-4-yl, phenyl, —$CONH_2$, —$CON(CH_3)_2$, $C_1$-$C_3$ alkyl, $C_1$-$C_3$ perfluorinated alkyl, —$CF_3$, —$OCF_3$, or $C_1$-$C_3$ alkoxy. In still other embodiments, M is iron (Fe), nickel (Ni), palladium (Pd), cadmium (Cd), manganese (Mn), cobalt (Co), copper (Cu), gallium (Ga), or zinc (Zn).

In some embodiments, $R^1$ is monovalent H, halogen, —CN, nitro (—NO$_2$), —NH$_2$, —N(CH$_3$)$_2$, hydroxy (—OH), methanoyl (—COH), carboxy (—CO$_2$H), $C_1$-$C_7$ alkyl, $C_1$-$C_6$ alkoxy, cycloalkyl, heterocyclyl, aryl, or heteroaryl, which —NH$_2$, —N(CH$_3$)$_2$, methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In certain embodiments, $R^1$ is H, $C_1$, Br, hydroxy (—OH), methanoyl (—COH), carboxy (—CO$_2$H), methyl, ethyl, n-propyl, or phenyl.

In other embodiments, $R^2$ is monovalent H, halogen, —CN, nitro (—NO$_2$), —NH$_2$, —N(CH$_3$)$_2$, hydroxy (—OH), methanoyl (—COH), carboxy (—CO$_2$H), $C_1$-$C_7$ alkyl, $C_1$-$C_6$ alkoxy, cycloalkyl, heterocyclyl, aryl, or heteroaryl, which —NH$_2$, —N(CH$_3$)$_2$, methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In yet other embodiments, $R^2$ is H, Cl, Br, hydroxy (—OH), methanoyl (—COH), carboxy (—CO$_2$H), methyl, ethyl, n-propyl, or phenyl.

In still other embodiments, $R^3$ is H, Cl, hydroxy (—OH), methyl, ethyl, $C_{1-5}$ alkyl, $C_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In yet other embodiments, $R^3$ is H, methyl, ethyl, n-propyl, or phenyl.

In certain embodiments, $R^4$ is H, Cl, hydroxy (—OH), methyl, ethyl, $C_{1-5}$ alkyl, $C_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, $R^4$ is H, methyl, ethyl, n-propyl, or phenyl.

In other embodiments, $R^3$ and $R^4$ are bonded together to form cyclobutyl, cyclopentyl, cyclohexyl, chlorocyclohexyl, fluorocyclohexyl, methoxycyclohexyl, ethoxycyclohexyl, methylcyclohexyl, trifluoromethylcyclohexyl, cycloheptyl, cyclooctyl, pyrrolidinyl, pyrrolinyl, imidazolidinyl, pyrazolidinyl, piperidyl, piperazinyl, indolinyl, morpholinyl, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, or methylenedioxyphenyl. In still other embodiments, $R^3$ and $R^4$ are not bonded together.

In certain embodiments, M is cadmium (Cd), manganese (Mn), gallium (Ga), or zinc (Zn). In certain embodiments, M is zinc (Zn).

In other embodiments, the solution solvent is selected from $CH_3CN$, water, a $C_1$-$C_8$ alcohol, methanol, ethanol, propanol, butanol, n-butanol, pentanol, hexanol, or a combination thereof. In some embodiments, the solution solvent is selected from $CH_3CN$, methanol, ethanol, propanol, n-butanol, pentanol, or a combination thereof.

In other embodiments, the acid has a pKa of no more than about 14. In certain embodiments, the acid is acetic acid, $Et_3NHBF_4$, piperidinium tetrafluoroborate, phosphoric acid, or a combination thereof. In some embodiments, the acid is acetic acid.

In other embodiments, the composition further comprises a hydride source. In still other embodiments, the composition further comprises a hydride source and the hydride source is a chemical hydride source or an electrochemical hydride source. In yet other embodiments, the composition further comprises a chemical hydride source and the chemical hydride source is a metal hydride, $NaBH_4$, or $LiAlH_4$. In some embodiments, the composition further comprises an electrochemical hydride source and the electrochemical hydride source is a platinum (Pt) electrode, a palladium (Pd) electrode, or a glassy carbon electrode.

In still other embodiments, the composition further comprises an electrode. In certain embodiments, the composition further comprises an electrode and the electrode is a platinum (Pt) electrode, a palladium (Pd) electrode, or a glassy carbon electrode.

In other embodiments, the temperature of the composition is from 0° C. to 99° C.

In some embodiments, the source of carbon dioxide is from air, from the waste gas of a powerplant, from the byproduct of a chemical reaction, from the byproduct of a catalytic reaction, or a combination thereof.

In certain embodiments, the source of the carbon dioxide is from a gas and the concentration of carbon dioxide in the gas is from about 0.01% to about 90%.

Certain embodiments of the invention include a method for producing formate from carbon dioxide comprising (1) contacting carbon dioxide with a first composition to provide a second composition, where the first composition comprises (a) a compound selected from Formula (I), salts, optical isomers, geometric isomers, salts of isomers, derivatives as disclosed herein, and solvent associated complexes thereof and (b) a solution solvent, and (2) adding acid to the second composition to produce formate.

Other embodiments of the invention are also discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
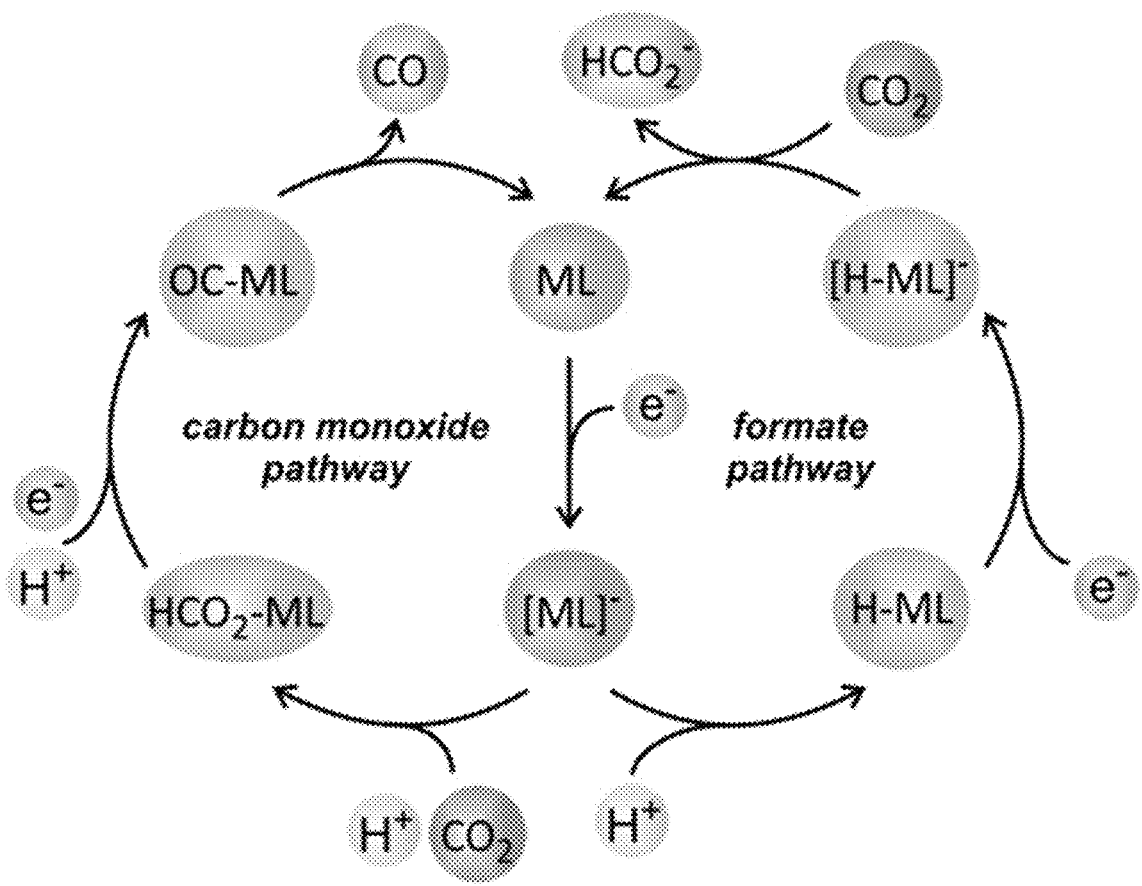
FIG. 1: A. An example of half-reactions for the two-electron reduction of $CO_2$. B. An example of pathways for catalytic reduction of $CO_2$ by two electrons.

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include methods of using a compound (e.g., Formula (I)) for the reduction of carbon dioxide to formate by contacting the carbon dioxide with a composition comprising a compound. In certain embodiments, the source of the carbon dioxide is air or is flue gas. Additional embodiments of the invention are also discussed herein.

As used herein (unless otherwise specified), the term "alkyl" means a monovalent, straight or branched hydrocarbon chain. For example, the terms "$C_1$-$C_7$ alkyl" or "$C_1$-$C_4$ alkyl" refer to straight- or branched-chain saturated hydrocarbon groups having from 1 to 7 (e.g., 1, 2, 3, 4, 5, 6, or 7), or 1 to 4 (e.g., 1, 2, 3, or 4), carbon atoms, respectively. Examples of $C_1$-$C_7$ alkyl groups include, but are not limited to, methyl, ethyl, n-propyl, i-propyl, n-butyl, s-butyl, t-butyl, n-pentyl, s-pentyl, n-hexyl, and n-septyl. Examples of $C_1$-$C_4$ alkyl groups include, but are not limited to, methyl, ethyl, n-propyl, i-propyl, n-butyl, s-butyl, and t-butyl.

As used herein (unless otherwise specified), the term "alkenyl" means a monovalent, straight or branched hydrocarbon chain that includes one or more (e.g., 1, 2, 3, or 4) double bonds. Examples of alkenyl groups include, but are not limited to, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, and 5-hexenyl.

As used herein (unless otherwise specified), the term "alkoxy" means any of the above alkyl groups which is attached to the remainder of the molecule by an oxygen atom (alkyl-O—). Examples of alkoxy groups include, but are not limited to, methoxy (sometimes shown as MeO—), ethoxy, isopropoxy, propoxy, and butyloxy.

As used herein (unless otherwise specified), the term "alkynyl" means a monovalent, straight or branched hydrocarbon chain that includes one or more (e.g., 1, 2, 3, or 4) triple bonds and that also may optionally include one or more (e.g. 1, 2, 3, or 4) double bonds in the chain. Examples of alkynyl groups include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

As used herein (unless otherwise specified), the term "aryl" means a monovalent, monocyclic or bicyclic, 5, 6, 7, 8, 9, 10, 11, or 12 membered aromatic hydrocarbon group which, when unsubstituted. Examples of aryl groups include, but are not limited to, phenyl, naphthyl, tolyl, and xylyl. For a bicyclic aryl that is designated as substituted, one or both rings can be substituted.

As used herein (unless otherwise specified), the term "cycloalkyl" means a monovalent, monocyclic or bicyclic, 3, 4, 5, 6, 7, 8, 9, 10, 11, or 12 membered hydrocarbon group. The rings can be saturated or partially unsaturated. Examples of cycloalkyl groups include, but are not limited to, cyclopropyl, cyclobutyl, cyclopentyl, cyclohexyl, cycloheptyl, cyclooctyl, and bicycloalkyls (e.g., bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds). For a monocyclic cycloalkyl, the ring is not aromatic. For a bicyclic cycloalkyl, if one ring is aromatic, then the other is not aromatic. For a bicyclic cycloalkyl that is designated as substituted, one or both rings can be substituted.

As used herein (unless otherwise specified), the term "halogen" means monovalent Cl, F, Br, or I.

As used herein (unless otherwise specified), the term "heteroaryl" means a monovalent, monocyclic or bicyclic, 5, 6, 7, 8, 9, 10, 11, or 12 membered, hydrocarbon group, where 1, 2, 3, 4, 5, or 6 carbon atoms are replaced by a hetero atom independently selected from nitrogen, oxygen, or sulfur atom, and the monocyclic or bicyclic ring system is aromatic. Examples of heteroaryl groups include, but are not limited to, thienyl (or thiophenyl), furyl, indolyl, pyrrolyl, pyridinyl, pyrazinyl, oxazolyl, thiaxolyl, quinolinyl, pyrimidinyl, imidazolyl, triazolyl, tetrazolyl, 1H-pyrazol-4-yl, 1-Me-pyrazol-4-yl, pyridin-3-yl, pyridin-4-yl, 3,5-dimethylisoxazolyl, 1H-pyrrol-3-yl, 3,5-di-Me-pyrazolyl, and 1H-pyrazol-4-yl. For a bicyclic heteroaryl, if one ring is aryl, then the other is heteroaryl. For a bicyclic heteroaryl, one or both rings can have one or more hetero atoms. For a bicyclic heteroaryl that is designated as substituted, one or both rings can be substituted.

As used herein (unless otherwise specified), the term "heterocyclyl" means a monovalent, monocyclic or bicyclic, 5, 6, 7, 8, 9, 10, 11, or 12 membered, hydrocarbon, where 1, 2, 3, 4, 5, or 6 carbon atoms are replaced by a hetero atom independently selected from nitrogen atom, oxygen atom, or sulfur atom, and the monocyclic or bicyclic ring system is not aromatic. Examples of heterocyclyl groups include, but are not limited to, tetrahydropyran, pyrolidinyl (e.g., pyrrolidin-1-yl, pyrrolidin-2-yl, pyrrolidin-3-yl, or pyrrolidin-4-yl), piperazinyl (e.g., piperazin-1-yl, piperazin-2-yl, piperazin-3-yl, or piperazin-4-yl), piperidinyl (e.g., piperadin-1-yl, piperadin-2-yl, piperadin-3-yl, or piperadin-4-yl), and morpholinyl (e.g., morpholin-1-yl, morpholin-2-yl, morpholin-3-yl, or morpholin-4-yl). For a bicyclic heterocyclyl, if one ring is aromatic (e.g., monocyclic aryl or heteroaryl), then the other ring is not aromatic. For a bicyclic heterocyclyl, one or both rings can have one or more hetero atoms. For a bicyclic heterocyclyl that is designated as substituted, one or both rings can be substituted.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

As used herein (unless otherwise specified), the term "substituted" (e.g., as in substituted alkyl) means that one or more hydrogen atoms of a chemical group (with one or more hydrogen atoms) can be replaced by one or more non-hydrogen substituents selected from the specified options. The replacement can occur at one or more positions. The term "optionally substituted" means that one or more hydrogen atoms of a chemical group (with one or more hydrogen atoms) can be, but is not required to be, substituted.

Some compounds of the invention can have one or more chiral centers and can exist in and be isolated in optically active and racemic forms, for any of the one or more chiral centers. Some compounds can exhibit polymorphism. The compounds of the present invention (e.g., Formula I) encompass any optically active, racemate, stereoisomer form, polymorphism, or mixtures thereof. If a chiral center does not provide an indication of its configuration (i.e., R or S) in a chemical structure, it should be considered to represent R, S or a racemate.

Compounds and Compositions

Some embodiments of the invention include compounds selected from Formula (I):

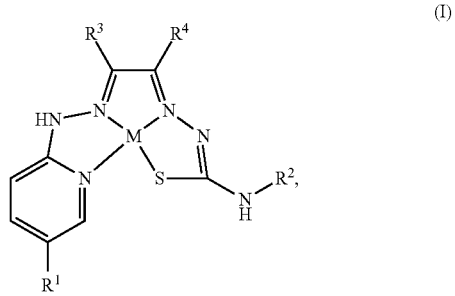

salts, optical isomers, geometric isomers, salts of isomers, and derivatives thereof.

In some embodiments, $R^1$ can be monovalent H, halogen (e.g., F, Cl, Br, or I), —CN, nitro (—NO$_2$), —NH$_2$, —N(CH$_3$)$_2$, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which —NH$_2$, —N(CH$_3$)$_2$, methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, $R^1$ can be monovalent H, halogen (e.g., F, Cl, Br, or I), —CN, nitro (—NO$_2$), —NH$_2$, —N(CH$_3$)$_2$, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, $R^1$ can be H, Cl, Br, hydroxy (—OH), methanoyl (—COH), carboxy (—CO$_2$H), methyl, ethyl, $C_{1-5}$ alkyl, $C_3$ alkyl (e.g., n-propyl or isopropyl), —CN, nitro (—NO$_2$), —NH$_2$, —N(CH$_3$)$_2$, ethynyl, —CONH$_2$, —CON(CH$_3$)$_2$, ethoxy, methoxy, or phenyl. In some embodiments, $R^1$ can be H, Cl, Br, hydroxy (—OH), methanoyl (—COH), carboxy (—CO$_2$H), methyl, ethyl, n-propyl, or phenyl.

In some embodiments, $R^2$ can be monovalent H, halogen (e.g., F, Cl, Br, or I), —CN, nitro (—NO$_2$), —NH$_2$, —N(CH$_3$)$_2$, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which —NH$_2$, —N(CH$_3$)$_2$, methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, R$^2$ can be monovalent H, halogen (e.g., F, Cl, Br, or I), —CN, nitro (—NO$_2$), —NH$_2$, —N(CH$_3$)$_2$, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In some embodiments, R$^2$ can be H, Cl, Br, hydroxy (—OH), methanoyl (—COH), carboxy (—CO$_2$H), methyl, ethyl, $C_1$-5 alkyl, $C_3$ alkyl(e.g., n-propyl or isopropyl), —CN, nitro (—NO$_2$), —NH$_2$, —N(CH$_3$)$_2$, ethynyl, —CONH$_2$, —CON(CH$_3$)$_2$, ethoxy, methoxy, or phenyl. In some embodiments, R$^2$ can be H, Cl, Br, hydroxy (—OH), methanoyl (—COH), carboxy (—CO$_2$H), methyl, ethyl, n-propyl, or phenyl.

In some embodiments, R$^3$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluoronated alkyl, —CF$_3$, —OCF$_3$, or $C_1$-$C_3$ alkoxy. In other embodiments, R$^3$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluorinated alkyl, —CF$_3$, —OCF$_3$, or $C_1$-$C_3$ alkoxy. In some embodiments, R$^3$ can be H, Cl, hydroxy (—OH), methyl, ethyl, $C_{15}$ alkyl, $C_3$ alkyl(e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^3$ can be H, methyl, ethyl, $C_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^3$ can be H, methyl, ethyl, n-propyl, or phenyl.

In some embodiments, R$^4$ can be monovalent H, halogen (e.g., F, Cl, Br, or I), —CN, hydroxy (—OH), methanoyl (—COH), carboxy (—CO$_2$H), $C_1$-$C_{10}$ alkyl (e.g., $C_1$, $C_2$, $C_3$, $C_4$, $C_5$, $C_6$, $C_7$, $C_8$, $C_9$, or $C_{10}$ alkyl), $C_2$-$C_{10}$ alkenyl (e.g., $C_2$, $C_3$, $C_4$, $C_5$, $C_6$, $C_7$, $C_8$, $C_9$, or $C_{10}$ alkenyl), $C_2$-$C_{10}$ alkynyl (e.g., $C_2$, $C_3$, $C_4$, $C_5$, $C_6$, $C_7$, $C_8$, $C_9$, or $C_{10}$ alkynyl), $C_1$-$C_9$ alkoxy (e.g., $C_1$, $C_2$, $C_3$, $C_4$, $C_5$, $C_6$, $C_7$, $C_8$, or $C_9$ alkoxy), cycloalkyl, heterocyclyl, aryl, or heteroaryl, which methanoyl (—COH), carboxy (—CO$_2$H), $C_1$-$C_{10}$ alkyl, $C_2$-$C_{10}$ alkenyl, $C_2$-$C_{10}$ alkynyl, $C_1$-$C_9$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, $C_1$-$C_3$ alkyl, $C_1$-$C_3$ perfluorinated alkyl, —CF$_3$, —OCF$_3$, or $C_1$-$C_3$ alkoxy. In other embodiments, R$^4$ can be monovalent H, halogen (e.g., F, Cl, Br, or I), —CN, hydroxy (—OH), methanoyl (—COH), carboxy (—CO$_2$H), $C_1$-$C_7$ alkyl (e.g., $C_1$, $C_2$, $C_3$, $C_4$, $C_5$, $C_6$, or $C_7$ alkyl), $C_1$-$C_6$ alkoxy (e.g., $C_1$, $C_2$, $C_3$, $C_4$, $C_5$, or $C_6$ alkoxy), cycloalkyl, heterocyclyl, aryl, or heteroaryl, which methanoyl (—COH), carboxy (—CO$_2$H), $C_1$-$C_7$ alkyl, $C_1$-$C_6$ alkoxy, cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —COmorpholin-4-yl, phenyl, —CONH$_2$, —CON(CH$_3$)$_2$, C$_1$-C$_3$ alkyl, C$_1$-C$_3$ perfluorinated alkyl, —CF$_3$, —OCF$_3$, or C$_1$-C$_3$ alkoxy. In some embodiments, R$^4$ can be H, Cl, hydroxy (—OH), methyl, ethyl, C$_{1-5}$ alkyl, C$_3$ alkyl(e.g., n-propyl or isopropyl), —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), 1,2-methylenedioxyphenyl, 2,3-methylenedioxyphenyl, furyl (e.g., 2-furyl), 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^4$ can be H, methyl, ethyl, C$_3$ alkyl, n-propyl, isopropyl, ethoxy, methoxy, 5-hydroxy pyridyl (e.g., 5-hydroxy pyrid-3-yl), indolyl (e.g., 1-indolyl), 1,2,3,4-tetrahydroisoquinolyl (e.g., 2-1,2,3,4-tetrahydroisoquinolyl), furyl (e.g., 2-furyl), 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl. In some embodiments, R$^4$ can be H, methyl, ethyl, n-propyl, or phenyl.

In other embodiments, R$^3$ and R$^4$ can be bonded together (with their attached carbons) to form a ring that is fused to the attached carbons of R$^3$ and R$^4$, where the ring that is fused can be cycloalkyl, heterocyclyl, aryl, or heteroaryl, which cycloalkyl, heterocyclyl, aryl, or heteroaryl can optionally be substituted with one or more (e.g., 0, 1, 2, 3, 4, 5, or 6) of halogen (e.g., F, Cl, Br, or I), oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluorinated alkyl, —CF$_3$, —OCF$_3$, or C$_1$-C$_3$ alkoxy. In some embodiments, R$^3$ and R$^4$ can be bonded together to form a ring that is fused to the attachments of R$^3$ and R$^4$, where the ring that is fused can be cyclobutyl, cyclopentyl, cyclohexyl, chlorocyclohexyl, fluorocyclohexyl, methoxycyclohexyl, ethoxycyclohexyl, methylcyclohexyl, trifluoromethylcyclohexyl, cycloheptyl, cyclooctyl, pyrrolidinyl, pyrrolinyl, imidazolidinyl, pyrazolidinyl, piperidyl, piperazinyl, indolinyl, morpholinyl, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, or methylenedioxyphenyl. In some embodiments, R$^3$ and R$^4$ are not bonded together.

In other embodiments, M can be any suitable divalent cation. In certain embodiments, M can be iron (Fe), nickel (Ni), palladium (Pd), cadmium (Cd), manganese (Mn), cobalt (Co), copper (Cu), gallium (Ga), or zinc (Zn). In some embodiments, M can be nickel (Ni), copper (Cu), cadmium (Cd), manganese (Mn), cobalt (Co), gallium (Ga), or zinc (Zn). In some embodiments, M can be cadmium (Cd), manganese (Mn), gallium (Ga), or zinc (Zn). In some embodiments, M can be zinc (Zn).

In some embodiments, the compounds of Formula (I) can be selected from those specified in Table 1.

TABLE 1

| Compound Number (alternative designation) | Compound Structure |
|---|---|
| I-1 (Zn(DMTH)) | *structure* |
| I-2 | *structure* |
| I-3 | *structure* |

TABLE 1-continued
| Compound Number (alternative designation) | Compound Structure |
|---|---|
| I-4 | 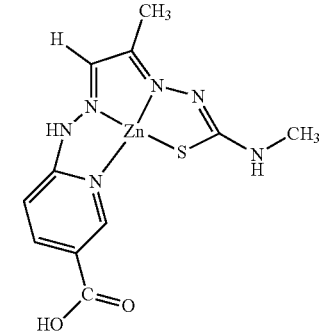 |
| I-5 | 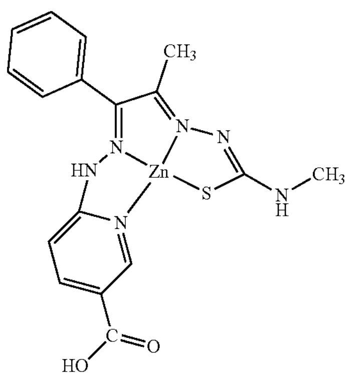 |
| I-6 | 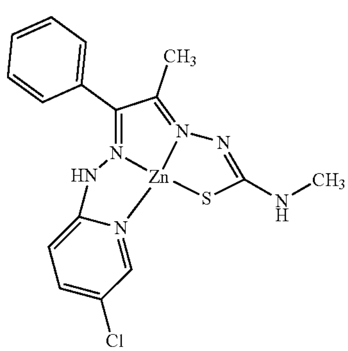 |
| I-7 | 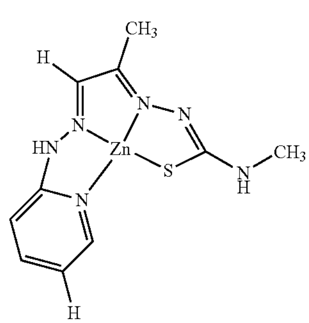 |
| I-8 | 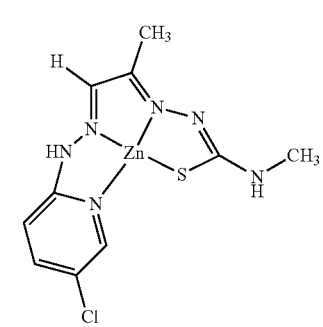 |
| I-9 | |
| I-10 | |
| I-11 | |

TABLE 1-continued

| Compound Number (alternative designation) | Compound Structure |
|---|---|
| I-12 | 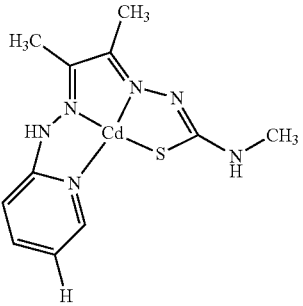 |

In some embodiments, the compounds of Formula (I) (e.g., I-1, I-2, I-3, I-4, I-5, I-6, I-7, I-8, I-9, I-10, I-11, or I-12) can be in the form of salts, optical and geometric isomers, and salts of isomers. In other embodiments, the compounds can be in various forms, such as uncharged molecules, components of molecular complexes, or salts, including but not limited to hydrochloride, hydrobromide, sulphate, phosphate, nitrate, borate, acetate, maleate, tartrate, salicylate, hexaflurophosphate, and tetrafluorborate. In some instances, for acidic compounds, salts can include metals, amines, or organic cations (e.g. quaternary ammonium). In yet other embodiments, the compound can be in the form of derivatives of Formula (I) (e.g., ethers, esters, or amides). In still other embodiments, the compounds can include 1, 2, or 3 solvent molecules associated with Formula (I), such as but not limited to water, methanol, ethanol, propanol, isopropanol, acetonitrile, dmf, 2-butoxyethoxyethyl acetate, n,n-dimethylacetamide, 2-butoxyethylacetate, n-formylmorpholine, 2-methoxyethyl acetate, 1,4-dioxane, acetone, acetylacetone, methyl acetate, 1-nitropropane, 2-nitropropane, isooctane, n-tert-butylyformamide, propylene carbonate, γ-butyrlactone, butyl lactate, 1,1,3,3-tetramethylurea, 1,3-dimethyl-2-imidazolidinone, and 1,3-dimethyl-3,4,5,6-tetrahydro-2(1H)-pyrimidinone; for example, solvent molecule association can occur when the compound is added to the solvent (e.g., neat solvent or solvent in a mixture)

In some embodiments, the compounds of the invention having a chiral center and can exist in and be isolated in optically active and racemic forms. In other embodiments, compounds may exhibit polymorphism. Some embodiments of the present invention encompass any racemic, optically active, polymorphic, or stereoisomeric form, or mixtures thereof, of a compound described herein. The preparation of optically active forms can be accomplished by any suitable method, including but not limited to, resolution of the racemic form by recrystallization techniques, synthesis from optically-active starting materials, chiral synthesis, or chromatographic separation using a chiral stationary phase.

In other embodiments, compounds of the invention encompass Formula (I) and salts, optical isomers, geometric isomers, salts of isomers, and derivatives thereof, and solvent associated complexes thereof.

The compounds discussed herein can be synthesized using any suitable method, including but not limited to those disclosed herein. In other embodiments, compound I-1 can be synthesized and characterized by previous reported methods, with slight modifications (e.g., (CALATAYUD et al., (2012) "Complexes of group 12 metals containing a hybrid thiosemicarbazone-pyridylhydrazone ligand" Inorg. Chim. Acta, Vol. 381, pp. 150-161)). In yet other embodiments, the ligand of compound I-1 can be prepared in two steps from 2,3-butanedione, 2-hydrazinopyridine, and 4-methylthiosemicarbazide (e.g., COWLEY et al. (2006) "Copper Complexes of Thiosemicarbazone-Pyridylhydrazine (THYNIC) Hybrid Ligands: A New Versatile Potential Bifunctional Chelator for Copper Radiopharmaceuticals" Inorg. Chem., Vol. 45, pp. 496-498.)) In still other embodiments, compound I-1 (with methanol as an associated solvent) can be prepared from the ligand and $Zn(OAc)_2 \cdot 2H_2O$ (e.g., CRONIN et al. (2019) "Utilizing Charge Effects and Minimizing Intramolecular Proton Rearrangement to Improve Overpotential of a Thiosemicarbazonato Zinc HER Catalysts" Inorg. Chem., Vol. 58, pp. 12986-12997). In some embodiments, compound I-1 (with water as an associated solvent) can be prepared from the ligand, LiOH (2 eq.) and $Zn(NO_3)_2 \cdot 6H_2O$; addition of only one eq. LiOH can allow isolation of the monoprotonated compound of I-1 (e.g., CALATAYUD et al. (2012) "Complexes of group 12 metals containing a hybrid thiosemicarbazone-pyridylhydrazone ligand" Inorg. Chim. Acta, Vol. 381, pp. 150-161). In still other embodiments, compound I-1 with an associated acetate salt can be prepared by adding acetic acid to compound I-1. In yet other embodiments, compound I-1 with an associated nitrate salt can be prepare by adding $Zn(NO_3)$ and LiOH (1 eq.) to the ligand of compound I-1. Any suitable method can be used to characterize and/or confirm the product identity including but not limited to mass spectrometry, cyclic voltammetry (CV), elemental analysis, and $^1H$ and $^{13}C$ NMR, FT-IR, and UV-visible spectroscopy. (COWLEY et al. (2006) "Copper Complexes of Thiosemicarbazone-Pyridylhydrazine (THYNIC) Hybrid Ligands: A New Versatile Potential Bifunctional Chelator for Copper Radiopharmaceuticals" Inorg. Chem., Vol. 45, pp. 496-498.)

Unless otherwise indicated, $L^1$ is the ligand of compound I-1, $L^2$ is the ligand of compound I-2, and so forth.

In certain embodiments, compounds of Formula (I) (e.g., compounds I-2 through I-9) can be prepared using any suitable method including but not limited to those described herein. In other embodiments, the ligand of compound I-2 can be prepared from 2-hydrazinopyrindine with 6-hydrazinonicotinic acid as previously reported (e.g., COWLEY et al. (2006) "Copper Complexes of Thiosemicarbazone-Pyridylhydrazine (THYNIC) Hybrid Ligands: A New Versatile Potential Bifunctional Chelator for Copper Radiopharmaceuticals" Inorg. Chem., Vol. 45, pp. 496-498.). In other embodiments, the ligand of compound I-3 can be prepared in a similar fashion to the ligands of compounds I-1 and I-2, from 2-hydrazino-5-methylpyridine, which can be prepared from commercially available 2-chloro-5-methylpyridine and hydrazine monohydrate (e.g., FINLAY et al. (2013) "Triazolo and imidazo dihydropyrazolopyrimidine potassium channel antagonists" Bioorg. Med. Chem. Lett., Vol. 23, pp. 1743-1747). In yet other embodiments, the ligands of compounds I-4 to I-6 can be prepared from pyruvic aldehyde dimethyl acetal by modification of methods to prepare $C_s$-symmetric BTSCs (Scheme 1) (e.g., BROWN et al., (2017) "Copper complexes with dissymmetrically substituted bis(thiosemicarbazone) ligands as a basis for PET radiopharmaceuticals: control of redox potential and lipophilicity" Dalton Trans., Vol. 46, pp. 14612-14630).

Scheme 1. Synthetic protocol for certain related ligands of compounds I-4 to I-6 (i.e., $H_2L^{4-6}$).

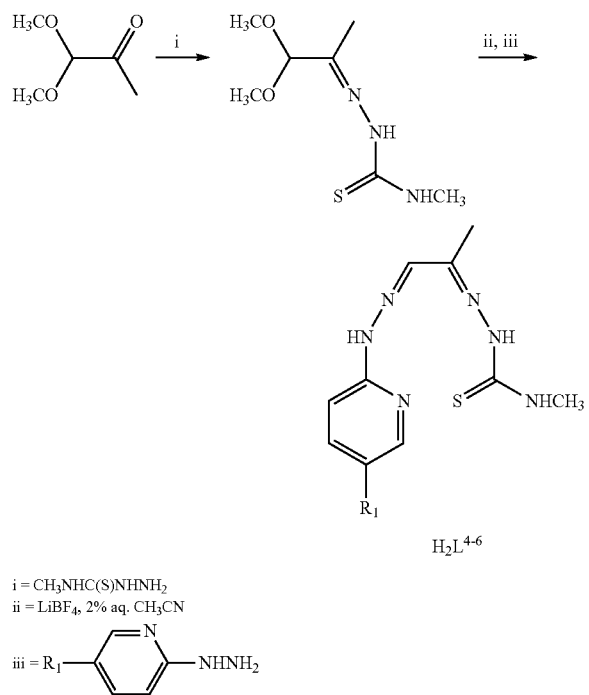

i = $CH_3NHC(S)NHNH_2$
ii = $LiBF_4$, 2% aq. $CH_3CN$

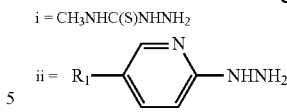

In yet other embodiments, the ligands of compounds I-7 to I-9 can be prepared from 1-phenylpropane-1,2-dione (Scheme 2) through modification of reported methods for similar diones. (HOLLAND et al. (2007) "Functionalized Bis(thiosemicarbazonato) Complexes of Zinc and Copper: Synthetic Platforms Toward Site-Specific Radiopharmaceuticals" Inorg. Chem., Vol. 46, pp. 465-485.)

Scheme 2. Synthetic protocol for certain related ligands of compounds I-7 to I-9 (i.e., $H_2L^{7-9}$).

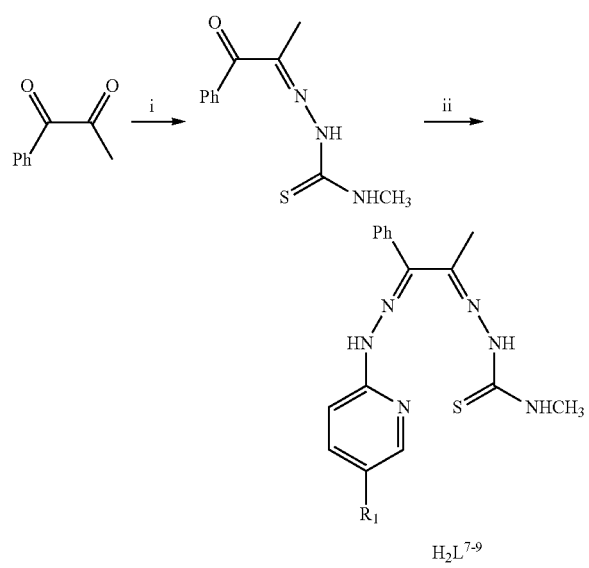

i = $CH_3NHC(S)NHNH_2$ ii = 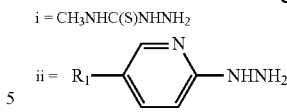

In some embodiments, condensation of 1-phenylpropane-1,2-dione with one equivalent of 4-methylthiosemicarbazide can occur selectively at the methyl ketone. A second condensation with the 2-hydrazinopyridines can allow isolation of the ligands of compounds I-6 to I-9. The ligands can be characterized using any suitable method including but not limited to by $^1H$ and $^{13}C$ NMR, FT-IR, mass spectrometry, and x-ray diffraction (e.g., single crystal).

From their ligands, compounds I-2 to I-9 can be prepared, isolated, and characterized using the same methods as compound I-1. Any suitable method can be used to prepare compounds with other $d^{10}$ (e.g., $Cd^{2+}$, $Ga^{3+}$) or $d^5$ (e.g., $Mn^{2+}$) metal ions.

Synthesis of the $Cd^{2+}$ compound $[Cd(HL^1)(NO_3)]_2$ can occur using any suitable method including but not limited to those used for $Zn^{2+}$. (CALATAYUD et al., (2012) "Complexes of group 12 metals containing a hybrid thiosemicarbazone-pyridylhydrazone ligand" Inorg. Chim. Acta, Vol. 381, pp. 150-161). In some embodiments, $CdL^1(CH_3OH)$ can be synthesized using methods described above for $ZnL^1(CH_3OH)$. In still other embodiments, the same or similar strategies can be employed to prepare the related pair of $Cd^{2+}$ compounds for ligands of compounds I-2 to 1-9. In certain embodiments, high-spin $Mn^{2+}$ compounds can be prepared by modification of the reported synthesis of the BTSC complexes $[Mn(H_2L^{N3,S2})(H_2O)_2](OAc)_2$. (LU et al., (2014) "Synthesis, Crystal Structure, and Biological Activity of an Mn(II) Complex Derived from 2,6-diacetylpyridine bis(N 4-methylthiosemicarbazone)" Synth. React. Inorg., Met.-Org., Nano-Met. Chem., Vol. 44, pp. 1068-1072; PEDRIDO et al., (2005) "Syntheses and X-ray characterization of metal complexes with the pentadentate thiosemicarbazone ligand bis(4-N-methylthiosemicarbazone)-2,6-diacetylpyridine. The first pentacoordinate lead(II) complex with a pentagonal geometry" Dalton Trans., pp. 572-579). In certain embodiments, inclusion of one or two equivalents of LiOH can be used to yield the octahedral compounds $[Mn(HL^{1-9})(CH_3OH)_2]^+$ and $Mn(L^{1-9})(CH_3OH)_2$. In other embodiments, the coordination of alcohol to the metal upon ligand deprotonation can occur (e.g., see the reported x-ray structure $Mn(L^{N3,S2})(CH_3CH_2OH)_2$ in PEDRIDO et al. (2008) "Pentadentate thiosemicarbazones as versatile chelating systems. A comparative structural study of their metallic complexes" Dalton Trans., pp. 6776-6787). In still other embodiments, the $Ga^{3+}$ compounds $Ga(L^1)(OCH_3)$ and $[Ga(HL^1)(NO_3)]NO_3$ can be prepared by modification of reported procedures for $N_2S_2$ BTSC complexes. (VENKATACHALAM et al. (2018) "A Novel Strategy to Introduce 18F, a Positron Emitting Radionuclide, into a Gallium Nitrate Complex: Synthesis, NMR, X-Ray Crystal Structure, and Preliminary Studies on Radiolabelling with 18F" Aust. J. Chem, Vol. 71, pp. 81-86; ARROWSMITH et al., (2011) "Fluorescent gallium and indium bis(thiosemicarbazonates) and their radiolabelled analogues: Synthesis, structures and cellular confocal fluorescence imaging investigations" Dalton Trans., Vol. 40, pp. 6238-6252). Any suitable method can be used to characterize the synthesized compounds including but not limited to by single crystal x-ray diffraction, mass spectrometry, CV, elemental analysis, and $^1$H and $^{13}$C NMR (except $Mn^{2+}$ compounds), FT-IR, and UV-visible spectroscopy.

In certain embodiments, one or more compounds discussed herein (e.g., Formula (I), I-1, I-2, I-3, I-4, I-5, I-6, I-7, I-8, I-9, I-10, I-11, or I-12) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds discussed herein (e.g., Formula (I), I-1, I-2, I-3, I-4, I-5, I-6, I-7, I-8, I-9, I-10, I-11, or I-12) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds discussed herein (e.g., Formula (I), I-1, I-2, I-3, I-4, I-5, I-6, I-7, I-8, I-9, I-10, I-11, or I-12).

In some embodiments, the composition can comprise a solvent, an acid or both. In certain embodiments, any suitable solvent (e.g., solution solvent) can be included in the composition including but not limited to an $CH_3CN$, water, a $C_1$-$C_8$ alcohol, methanol, ethanol, propanol, butanol (e.g., n-butanol), pentanol, hexanol, or a combination thereof. In some embodiments, the solvent (e.g., solution solvent) comprises at least an alcohol (e.g., a $C_1$-$C_8$ alcohol, methanol, ethanol, propanol, butanol (e.g., n-butanol), pentanol, hexanol, or a combination thereof) and optionally $CH_3CN$, water, or a combination thereof. In other embodiments, any suitable acid can be included in the composition including but not limited to an acid with a weak acid, acetic acid, $Et_3NHBF_4$, piperidinium tetrafluoroborate, phosphoric acid, or a combination thereof. In certain embodiments, the pKa of the acid is no more than about 14, no more than about 13, no more than about 12, no more than about 11.5, no more than about 11, no more than about 10, no more than about 8, or no more than about 6. In yet other embodiments, the pKa of the acid is within about +/−0.1 pH unit, about +/−0.5 pH unit, about +/−1 pH, about +/−1 pH unit, about +/−2 pH unit, about +/−4 pH unit, about +/−6 pH unit, about +/−8 pH unit, about +/−9 pH unit of the pKa of the metal hydride of the metal in the compound of Formula (I). In yet other embodiments, the concentration of the acid can be about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 50 mM, about 100 mM, about 250 mM, from about 0.1 mM to about 250 mM, from about 0.1 mM to about 100 mM, from about 0.1 mM to about 50 mM, from about 0.1 mM to about 20 mM, from about 1 mM to about 250 mM, from about 1 mM to about 100 mM, from about 1 mM to about 50 mM, from about 1 mM to about 20 mM, no more than about 250 mM, no more than about 100 mM, no more than about 50 mM, no more than about 20 mM, or no more than about 10 mM. In other embodiments, any suitable electrolyte (e.g., supporting electrolytes) can be included in the composition including but not limited to tetraalkylammonium salts, tetraethylammonium salts, tetraproylammonium salts, tetrabutylammonium salts, tetrabutylammonium acetate, tetrabutylammonium benzoate, tetrabutylammonium bis-trifluoromethanesulfonimidate, tetrabutylammonium hexafluorophosphate, tetraethylammonium hexafluorophosphate, simple ionic electrolytes, group 1 or ammonium halides (e.g., NaCl, KCl, NaBr, or KBr), group 1 or ammonium perchlorates (e.g., $NaClO_4$ or $KClO_4$), group 1 or ammonium biphosphates (e.g., $NaH_2PO_4$), group 1 or ammonium tetrafluroborates (e.g., $NaBF_4$), group 1 or ammonium hexaflurophosphates (e.g., $NaPF_6$), group 1 or ammonium tosylates (e.g., NaOTs), group 1 or ammonium borates (e.g., $Na_2B_4O_7$), group 1 or ammonium bicarbonates (e.g., $NaHCO_3$), group 1 hydroxides (e.g., NaOH), group 1 or ammonium hydrogen phosphates (e.g., $Na_2H_2PO_4$), or group 1 or ammonium bisulfates (e.g., $NaHSO_4$). In some embodiments, any suitable source of hydride can be provided to the composition (chemical or electrochemical). In certain embodiments, a chemical hydride can be added to the composition, such as but not limited to metal hydrides, $NaBH_4$, $LiAlH_4$, diisobutylaluminium hydride (DIBAL), Tris(trimethylsilyl)silane, LiAB (lithium ammonium borane), NaAB (sodium ammonium borane), or $NH_3BH_3$. In other embodiments, the source of hydride can be electrochemical and can be achieved using an electrode, such as but not limited to using a Pt electrode, a Pd electrode, or a glassy carbon electrode. In other embodiments, the composition further comprises an electrode (e.g., which may provide a source of hydride or may not provide a source of hydride) and the electrode can be but is not limited to a Pt electrode, a Pd electrode, or a glassy carbon electrode. In still other embodiments, the temperature of the composition can be about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 96° C., about 97° C., about 98° C., about 99° C., about 99.5° C., about 100° C., about 101° C., about 102° C., about 103° C., about 104° C., about 105° C., about 110° C., from about 0° C. to about 100° C., from about 0° C. to about 90° C., from about 15° C. to about 100° C., or from about 15° C. to about 90° C.

In some embodiments, a compound of Formula (I) is part of a composition that is a homogenous solution, a homogenous aqueous solution, a heterogeneous solution, or a heterogeneous aqueous solution. In other embodiments, a homogenous solution, a homogenous aqueous solution, a heterogeneous solution, or a heterogeneous aqueous solution, each comprise a compound of Formula (I).

Methods

Certain embodiments of the invention include a method for reducing $CO_2$ to produce formate comprising contacting $CO_2$ with composition comprising a compound (e.g., Formula (I), I-1, I-2, I-3, I-4, I-5, I-6, I-7, I-8, I-9, I-10, I-11, or I-12), such as but not limited to compositions disclosed herein. In some embodiments of the method, the composition can comprise a solvent (e.g., solution solvent), an acid or both. In other embodiments, $CO_2$ is contacted with a composition comprising solvent (e.g., solution solvent), and then acid is added (e.g., admixed, mixed, injected, etc.). In yet other embodiments, the optional source of hydride or optional electrode can be added before, during, or after acid is added.

Some embodiments of the invention include a method for producing formate from carbon dioxide comprising (1) contacting carbon dioxide with a first composition to provide a second composition, where the first composition (e.g., such as but not limited to compositions disclosed herein) comprises (a) a compound (e.g., Formula (I), I-1, I-2, I-3, I-4, I-5, I-6, I-7, I-8, I-9, I-10, I-11, or I-12), and (b) a solvent (e.g., solution solvent), followed by (2) adding (e.g., admixing, mixing, injecting, etc.) acid to the second composition to produce formate. In yet other embodiments, the optional source of hydride or optional electrode can be added before, during, or after step (1) or before, during, or after step (2). In still other embodiments, the first composition does not comprise acid. In other embodiments, the second composition does not comprise acid prior to step (2).

Contacting (or any other grammatical or verb tense form such as "contacted" or "contact") in any of the methods disclosed herein can be any suitable form of contacting such as but not limited to bubbling gas into a solution, mixing (e.g., mixing a solution with dissolved gas), admixing (e.g., admixing a solution with dissolved gas), or injecting (e.g., injecting a solution with dissolved gas). Adding (or any other grammatical or verb tense form such as "added" or "add") in any of the methods disclosed herein can be any suitable form of adding, including but not limited to admixing, mixing, or injecting.

In certain embodiments, any suitable solvent (e.g., solution solvent) can be used in the methods including but not limited to an $CH_3CN$, water, a $C_1$-$C_8$ alcohol, methanol, ethanol, propanol, butanol (e.g., n-butanol), pentanol, hexanol, or a combination thereof. In some embodiments, the solvent (e.g., solution solvent) comprises at least an alcohol (e.g., a $C_1$-$C_8$ alcohol, methanol, ethanol, propanol, butanol (e.g., n-butanol), pentanol, hexanol, or a combination thereof) and optionally $CH_3CN$, water, or a combination thereof. In other embodiments, any suitable acid can be used in the methods including but not limited to an acid, a weak acid, acetic acid, $Et_3NHBF_4$, piperidinium tetrafluoroborate, phosphoric acid, or a combination thereof. In certain embodiments, the pKa of the acid is no more than about 14, no more than about 13, no more than about 12, no more than about 11.5, no more than about 11, no more than about 10, no more than about 8, or no more than about 6. In yet other embodiments, the pKa of the acid is within about +/−0.1 pH unit, about +/−0.5 pH unit, about +/−1 pH, about +/−1 pH unit, about +/−2 pH unit, about +/−4 pH unit, about +/−6 pH unit, about +/−8 pH unit, about +/−9 pH unit of the pKa of the metal hydride of the metal of the compound of Formula (I). In yet other embodiments, the concentration of the acid can be about 0.1 mM, about 0.5 mM, about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 20 mM, about 50 mM, about 100 mM, about 250 mM, from about 0.1 mM to about 250 mM, from about 0.1 mM to about 100 mM, from about 0.1 mM to about 50 mM, from about 0.1 mM to about 20 mM, from about 1 mM to about 250 mM, from about 1 mM to about 100 mM, from about 1 mM to about 50 mM, from about 1 mM to about 20 mM, no more than about 250 mM, no more than about 100 mM, no more than about 50 mM, no more than about 20 mM, or no more than about 10 mM. In other embodiments, any suitable electrolyte (e.g., supporting electrolytes) can be included in the composition (e.g., the first composition or the second composition) including but not limited to tetraalkylammonium salts, tetraethylammonium salts, tetraproylammonium salts, tetrabutylammonium salts, tetrabutylammonium acetate, tetrabutylammonium benzoate, tetrabutylammonium bis-trifluoromethanesulfonimidate, tetrabutylammonium hexafluorophosphate, tetraethylammonium hexafluorophosphate, simple ionic electrolytes, group 1 or ammonium halides (e.g., NaCl, KCl, NaBr, or KBr), group 1 or ammonium perchlorates (e.g., $NaClO_4$ or $KClO_4$), group 1 or ammonium biphosphates (e.g., $NaH_2PO_4$), group 1 or ammonium tetrafluroborates (e.g., $NaBF_4$), group 1 or ammonium hexaflurophosphates (e.g., $NaPF_6$), group 1 or ammonium tosylates (e.g., NaOTs), group 1 or ammonium borates (e.g., $Na_2B_4O_7$), group 1 or ammonium bicarbonates (e.g., $NaHCO_3$), group 1 hydroxides (e.g., NaOH), group 1 or ammonium hydrogen phosphates (e.g., $Na_2H_2PO_4$), or group 1 or ammonium bisulfates (e.g., $NaHSO_4$). In some embodiments, any suitable source of hydride (e.g., chemical or electrochemical) can be provided to the composition (e.g., the first composition, the second composition or both, and which can be the same or different for each composition). In certain embodiments, a chemical hydride can be added to the composition (e.g., the first composition, the second composition or both, and which can be the same or different for each composition), such as but not limited to metal hydrides, $NaBH_4$, $LiAlH_4$, diisobutylaluminium hydride (DIBAL), Tris(trimethylsilyl)silane, LiAB (lithium ammonium borane), NaAB (sodium ammonium borane), or $NH_3BH_3$. In other embodiments, the source of hydride can be electrochemical and can be achieved using an electrode, such as but not limited to using a Pt electrode, a Pd electrode, or a glassy carbon electrode. In other embodiments, the composition (e.g., the first composition, the second composition, or both) further comprises an electrode (e.g., which may provide a source of hydride or may not provide a source of hydride) and the electrode can be but is not limited to a Pt electrode, a Pd electrode, or a glassy carbon electrode. In still other embodiments, the temperature of the composition (e.g., the first composition, the second composition, or both) can be about −10° C., about −5° C., about 0° C., about 5° C., about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., about 96° C., about 97° C., about 98° C., about 99° C., about 99.5° C., about 100° C., about 101° C., about 102° C., about 103° C., about 104° C., about 105° C., about 110° C., from about 0° C. to about 100° C., from about 0° C. to about 90° C., from about 15° C. to about 100° C., or from about 15° C. to about 90° C.

In certain embodiments, the source of carbon dioxide is from air, from the waste gas of a powerplant, from the byproduct of a chemical reaction, from the byproduct of a catalytic reaction, or a combination thereof. In some embodiments, the source of the carbon dioxide is from a gas and the concentration of carbon dioxide in the gas (in % volume) is about 0.0001, about 0.001, about 0.01, about 0.02, about 0.03, about 0.04, about 0.05, about 0.06, about 0.07, about 0.08, about 0.09, about 0.1, about 0.2, about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 35, about 40, about 45, about 50, about 75, about 90, about 95, about 99, about 100, from about 0.0001 to about 100, from about 0.001 to about 100, from about 0.01 to about 100, from about 1 to about 100, from about 0.0001 to about 90, from about 0.001 to about 90, from about 0.01 to about 90, from about 1 to about 90, from about 0.0001 to about 50, from about 0.001 to about 50, from about 0.01 to about 50, from about 1 to about 50, from about 0.0001 to about 30, from about 0.001 to about 30, from about 0.01 to about 30, from about 1 to about 30, at least about 0.001, at least about 0.01, at least about 0.02, at least about 0.03, at least about 0.04, at least about 0.05, at least about 0.1, or at least about 1.

In some embodiments of the methods, the compound of formula (I) does not need to be reduced during the method. In other embodiments of the method, there is no need to pre-treat the gas (e.g., air or flue gas) prior to the contacting (e.g., prior to contacting the composition, the first composition, or the second composition).

The presently-disclosed subject matter is further illustrated by the following specific but non-limiting examples. The following examples may include compilations of data that are representative of data gathered at various times during the course of development and experimentation related to the present invention.

EXAMPLES

Materials and Methods

All reagents were obtained from commercially available sources and used as received unless otherwise noted. Solvents were dried and purified using an MBraun solvent purification system, except methanol which was dried using magnesium and iodide and then stored over molecular sieves. The compounds in this study are air and water stable as solids and were handled on the benchtop with no required protection from the atmosphere unless noted. Zn(DMTH) was synthesized and characterized by previous reported methods, with slight modifications (e.g., (CALATAYUD et al., (2012) "Complexes of group 12 metals containing a hybrid thiosemicarbazone-pyridylhydrazone ligand" Inorg. Chim. Acta, Vol. 381, pp. 150-161). The solid was collected as the dihydrate and placed under vacuum to dry. The container of Zn(DMTH) was subjected to flame drying prior to storage and use. The solid is red in color after flame drying, while its initial color is orange.

All experiments with pure $CO_2$ were conducted by passing $CO_2$ through a drying column filled with $CaSO_4$. For experiments using air as the $CO_2$ source, an Uniclife air pump UL40 purchased from Amazon was used. The pump has two ports, one of which was sealed with parafilm. The other port was connected to a piece of tygon tubing first sealed with parafilm and then fitted with a nozzle containing a needle that was inserted into the septum on the reaction vessel. The pump was operated at its highest setting for all experiments.

Physical Methods

All $^1H$ NMRs were done using DMSO-$d_6$ as a solvent on a 500 MHz Bruker NMR spectrometer. Infrared spectra were recorded on freshly prepared crystalline sample using a Nicolet 360 FT-IR with a smart iTR attachment. UV-vis spectra were obtained on 0.1 mM solutions of Zn(DMTH) in dry methanol using a Variant Cary 50 Bio with fast scan capabilities. To determine the equilibrium binding constant, various concentrations of $CO_2$ were bubbled through the solutions for 30 min prior to recording the spectra. Acid titration studies were conducted using 0.1M acetic acid in methanol.

Electrochemical Methods

All cyclic voltammetry (CV) and controlled potential coulometry (CPC) measurements were recorded using a Gamry Interface potentiostat/galvanostat connected to a glassy carbon working electrode (3.0 mm diameter, surface area=0.071 cm$^2$), a platinum auxillary electrode and Ag/Ag$^+$ reference electrode. Before use, the working electrode was polished using an aqueous alumina slurry. The working and counter electrodes were rinsed with ethanol, acetone, DI water and finally methanol or methanol/acetonitrile, followed by sonication for 15 min in methanol or methanol/acetonitrile. CV experiments were conducted using a five-neck electrochemical cell. Separate necks were used for the three electrodes. The remaining necks were used to maintain a constant Ar or $CO_2$ atmosphere during data acquisition and to introduce solids, acids, and adjust solvent levels. Solutions were purged with Ar gas to remove oxygen and prior recording initial voltammograms of the complex. $CO_2$ was then bubbled through the solutions for 15 min prior to recording voltammograms for each experiment. All data presented are background subtracted. CPC measurements were conducted to determine faradaic efficiencies and were performed using a U-shaped tube containing a frit to separate the two compartments. The working compartment contained a glassy carbon or platinum electrode and an Ag/Ag$^+$ reference electrode. The counter electrode compartment was fitted with a platinum wire. All CV and CPC measurements were performed using solutions containing 0.1M Bu4NPF6 in methanol or 9:1 acetonitrile:methanol and 1mM Zn(DMTH). Ferrocene was used as an internal standard and added at the end of each experiment. For concentration dependent studies, a fresh solution for each concentration of complex was used. Prior to each CPC study a cyclic voltammogram of the complex was recorded. Potentials were then chosen from the potential of the catalytic peak. Following CPC studies, 100 μL of the reaction solution was transferred to an NMR tube containing 10 μL of DMF (standard solution which is calibrated to 30 mM) as an internal standard and 600 μL of DMSO-$d_6$. NMR spectra were recorded at a minimum of 128 scans with a 2 second relaxation delay. It should be explicitly noted that $CO_2$ or air is always added prior to the addition of acid in catalytic studies.

All calculations of overpotential and turnover frequency were done in the manner described by Haddad et. al. (HADDAD et al. (2017) "Metal-Assisted Ligand-Centered Electrocatalytic Hydrogen Evolution upon Reduction of a Bis(thiosemicarbazonato)Cu(II) Complex" Inorg. Chem., Vol. 56, pp. 11254-11265) and Fourmond et. al. (FOURMOND et al. (2010) "$H_2$ Evolution and Molecular Electrocatalysts: Determination of Overpotentials and Effect of Homoconjugation" Inorg. Chem., Vol. 49, pp. 10338-10347). The faradaic efficiency for formation of formate was confirmed by $^1H$ NMR and mmol quantity generated was determined based on integration against a 30 mM DMF standard. The total number of coulombs passed during CPE was corrected by subtracting the coulombs associated with a blank solution and used to determine the theoretical amount of formate that should be produced in mM. The following formula was used to determine the faradaic efficiency.

$$\text{Faradaic efficiency} = \frac{\text{Actual moles of HCO}_2^-}{\text{Theoretical moles of HCO}_2^-} \times 100\%$$

For isotopic labeling studies, a 5 L tank of $^{13}CO_2$ was purchased from Cambridge Isotopes. This tank was connected through swagelocks and a regulator to the airtight electrochemical cell containing 0.1 M $NBu_4PF_6$ and 1.0 mM Zn(DMTH) in methanol. This cell contained a working glassy carbon and a Ag/AgCl reference. The flow rate adjusted to 10.0 cc/min. and the cell was purged with the $^{13}CO_2$ for 15 minutes. Then, 8.3 mM acetic acid was added to the solution and it was stirred. The counter compartment containing 0.1 M $NBu_4PF_6$ in methanol and a platinum mesh electrode was placed as close to the working cell as possible. The solution was held at −2.30 V vs Fc/Fc$^+$ for 2 hours using a Biologic SP200. A 500 μL aliquot of this solution was removed and added to 100 μL of DMSO-$d_6$ and a $^1H$ NMR spectrum was recorded.

Crystallographic Studies

An h-tube was flame dried prior to addition of 0.004 g, 0.012 mmol of Zn(DMTH) and the tube was sealed with a septum then wired with copper. Ten milliliters of a 50:50 mixture of dried methanol and acetone was added to the tube to dissolve Zn(DMTH). It was done with great care, so that the solution stayed in the vertical portion of the h tube, and solvent levels didn't go larger than shoulder of the h. $CO_2$ was passed through a drying tube prior to bubbling in the Zn(DMTH) solution for 15 min. Further the headspace of the tube was filled with pure $CO_2$. The portion after the shoulder of the h tube was submerged in an ice bath. This ice bath was changed every 24 h, and yellow x-ray quality crystals of Zn(HDMTH)($CO_3CH_3$) were obtained after 5 days.

Reaction of Zn(DMTH) with $CO_2$ and $NaBH_4$ in MeOH

Zn(DMTH) (0.0066 g, 2.0 mM) was added to a 50 mL round bottom flask. This flask was then flame dried and filled with 10 mL of dry methanol. The methanol solution was stirred for 5 min to make sure all of the Zn complex had dissolved. Then the solution was bubbled with dry $CO_2$ for 15 min to ensure saturation. In a second flame dried flask, 0.3783 g (10.00 mmol) of $NaBH_4$ was dissolved in 2 mL of MeOH. The solution was transferred to the flask containing the Zn complex using a syringe and the mixture was stirred for 30 minutes under a stream of $CO_2$. A control was conducted in the absence of Zn(DMTH).

Results

The two-electron reduction of $CO_2$ in the presence of a proton donor can yield $HCO_2^-$ or carbon monoxide (CO) (FIG. 1A) through, for example, pathways shown in FIG. 1B. In these pathways, reduction occurs prior to $CO_2$ binding, which can sometimes limit their ability to fix $CO_2$ (e.g., at low concentrations of $CO_2$). No catalyst following these pathways can reduce $CO_2$ from air or 3-13% streams commonly found in power plant exhaust. Some embodiments of the invention include methods that do not use the pathway in FIG. 1B and that can reduce $CO_2$ from air or 3-13% streams.

Figure 2:
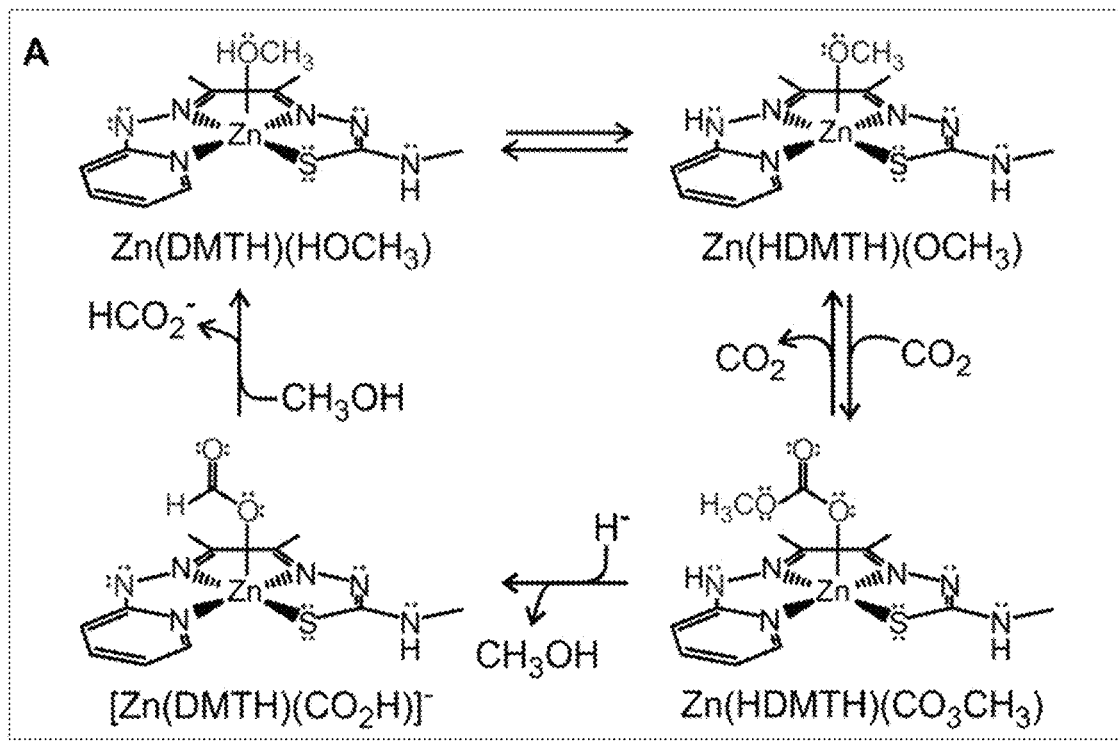
FIG. 2: A. An embodiment of a catalytic pathway for the reduction of $CO_2$ to $HCO_2^-$ by Zn(DMTH). The source of the hydride ($H^-$) can be chemical or electrochemical. All non-coordinating lone-pair electrons are shown. B. Representation of Zn(DMTH) highlighting the frustrated Lewis pair between the non-coordinating Lewis base (red) and Lewis acid (blue). Formal charges are shown in green. C. Addition of methanol across the frustrated Lewis pair via metal-ligand cooperativity.
Figure 2:
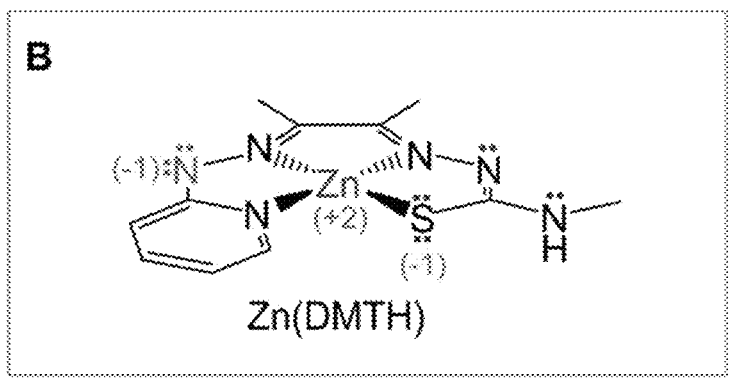
Figure 2:
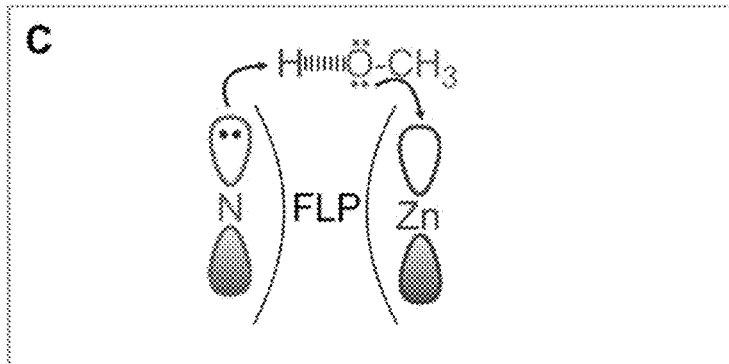

Without being bound by theory, the following proposed mechanism for some aspects of the catalytic activity for certain embodiments of the invention is discussed: The reduction of $CO_2$ to $HCO_2^-$ by Zn(DMTH) can follow a mechanism employing metal-ligand cooperativity (FIG. 2A). The catalyst can sometimes contain a frustrated Lewis pair (FLP) (e.g., see, STEPHAN (2016) "The broadening reach of frustrated Lewis pair chemistry" Science, Vol. 354, pp. 1248-1256) between the Zn(II) ion (Lewis acid) and the non-coordinating nitrogen of the 2-pyridinehydrazonato group (Lewis base) (FIG. 2B). The FLP can sometimes facilitate deprotonation of methanol ($CH_3OH$) to generate the active catalyst Zn(HDMTH)($OCH_3$) in equilibrium with Zn(DMTH)($HOCH_3$) (FIG. 2C). Insertion of $CO_2$ into the Zn—$OCH_3$ bond can yield a stable methylcarbonate intermediate Zn(HDMTH)($CO_3CH_3$). The methylcarbonate can provide an activated form of $CO_2$ that is susceptible to reduction by hydride generating $HCO_2^-$ and $CH_3OH$. The hydride source can be chemically ($NaBH_4$) or electrochemically generated from Pt or Zn(DMTH). Ligand substitution of $CH_3OH$ for $HCO_2^-$ can regenerate Zn(DMTH)($HOCH_3$) to complete the cycle. Alternate mechanistic routes (e.g., via C—O isomerization) may also occur.

Figure 3:
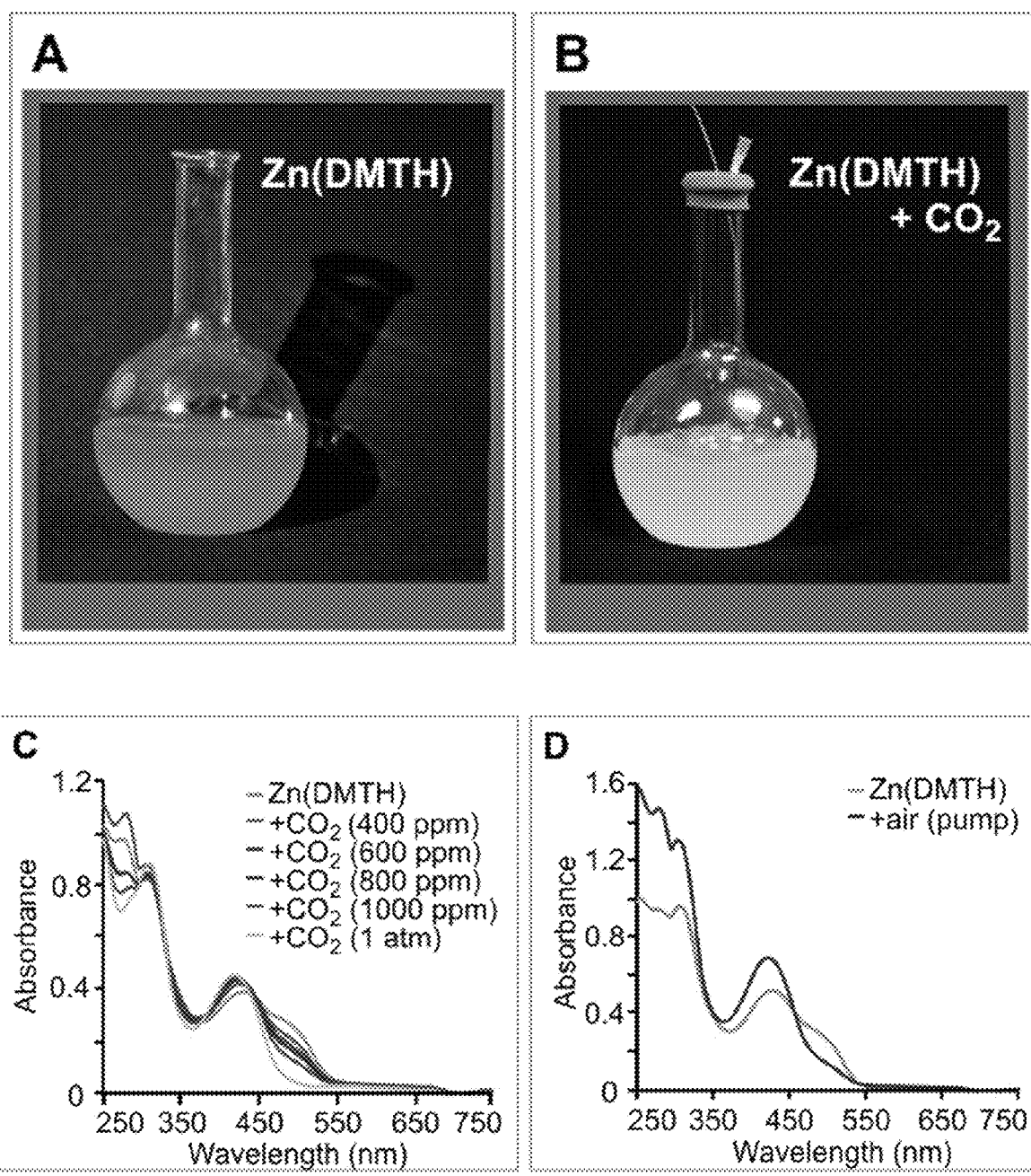
FIG. 3: A. Photograph of a 3 mM solution of Zn(DMTH) in methanol under ambient conditions. B. Photograph of a 3 mM solution of Zn(DMTH) in methanol, while bubbling with $CO_2$. C. UV-visible spectra of a 0.1 mM solution of Zn(DMTH) in methanol under varying concentrations of $CO_2$ gas. D. UV-visible spectra of a 0.1 mM solution of Zn(DMTH) in methanol before and after bubbling the solution with untreated air from the laboratory using an air pump.

In some embodiments of the invention, Zn(DMTH) can bind $CO_2$ prior to reduction. For example, in methanol, Zn(DMTH)($CH_3OH$) yields a bright orange solution (FIG. 3A) that changes to bright yellow upon bubbling with $CO_2$ (FIG. 3B). The solution returns to the original orange color when sparged with an inert gas ($N_2$ or Ar). The reversible $CO_2$ binding to Zn(DMTH)($CH_3OH$) can also be observed by changes in cyclic voltammetry (CV). In methanol, the CV of Zn(DMTH)($CH_3OH$) displays an irreversible reduction event with peak cathodic current ($E_{pc}$) at −1.77 V and an irreversible oxidation with peak anodic current ($E_{pa}$) at −0.06 V, vs. Fc+/Fc, at a scan rate of 200 mV/s. Introduction of $CO_2$ shifts the reduction peak anodically to −1.66 V and a pre-peak develops at −1.23 V. Analysis of the peak currents at −1.23 V and −1.66 V as a function of catalyst concentration show that both are first order with respect to catalyst indicating that Zn(HDMTH)($CO_3CH_3$) formation occurs via $CO_2$ insertion into Zn(DMTH)($CH_3OH$) through internal proton rearrangement. Sparging with an inert gas restores the initial CV confirming that $CO_2$ fixation is reversible.

To quantify the $CO_2$ binding affinity, UV-visible spectra were recorded using different concentrations of $CO_2$ (FIG. 3C). In the absence of $CO_2$, the UV-visible spectrum of Zn(DMTH)($CH_3OH$) shows a peak at 424 nm and a peak at 309 nm with a shoulder at 500 nm. Bubbling with 100% $CO_2$ results in a shift of the lower energy peak to 420 nm and loss of the shoulder at 500 nm. At lower $CO_2$ concentrations (400-1000 ppm), the intensity of the shoulder at 500 nm varies as a function of $CO_2$ concentration. Analysis of the data provides a $CO_2$ binding constant (K) of $(6.9\pm1.8)\times10^3$. Based on our measured value of K, Zn(DMTH) should be able to bind $CO_2$ from air (~415 ppm) in methanol. To confirm this, an air pump was used to introduce non-purified air from the surroundings into solutions of the complex (FIG. 3D). The results demonstrate the ability of Zn(DMTH) to sequester $CO_2$ from the atmosphere without first reducing the catalysts or pre-treating the air sample.

Figure 4:
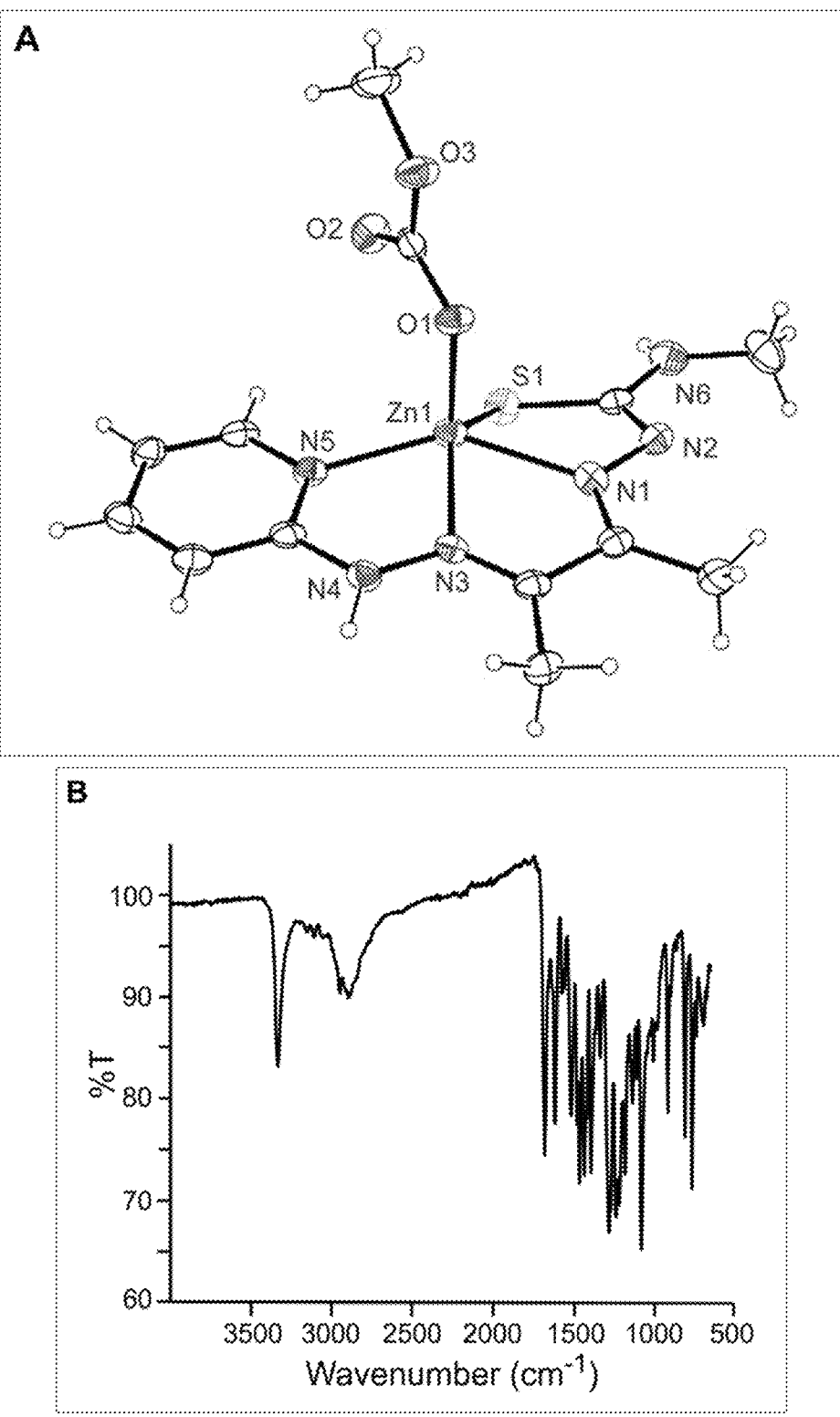
FIG. 4: A. ORTEP representation of [Zn(HDMTH)($CO_3CH_3$)]. B. FT-IR of [Zn(HDMTH)($CO_3CH_3$)] from single crystals.

The $CO_2$ bound complex was identified as the methylcarbonate intermediate, Zn(HDMTH)($CO_3CH_3$), by single crystal x-ray diffraction (FIG. 4A). The Zn(II) ion sits in a distorted square pyramidal arrangement with the $N_3S$ donors of (HDMTH)-chelate in the equatorial plane and a methylcarbonate in the apical position. The hydrogen atom $H_4N$ on the 2-pyridinehydrazonato nitrogen N4 was located in the electron difference map. The methylcarbonate is coordinated to Zn through the formally anionic O1 with a Zn—O1 distance of 1.991(3) Å. The planarity of the carbonate carbon, C12, is consistent with a change in hybridization to sp$^2$ from sp in $CO_2$. The infrared spectrum of Zn(HDMTH)($CO_3CH_3$) crystals further confirms the fixation of $CO_2$ as a methylcarbonate with concomitant protonation of the 2-pyridinehydrazonato nitrogen (FIG. 4B). The infrared spectra of monoalkylcarbonato zinc(II) complexes display characteristic v1 and v2 stretching vibrations near 1650 and 1300 $cm^{-1}$, respectively, and an out-of-plane bending mode ($\pi$) at ~810 $cm^{-1}$. These bands are present in the spectrum of Zn(HDMTH)($CO_3CH_3$) as an intense band at 1681 $cm^{-1}$, a shoulder at 1298 $cm^{-1}$, and a peak at 814 $cm^{-1}$. The protonation of the 2-pyridinehydrazonato nitrogen is confirmed by the appearance of a broad N—H stretch at 2889 $cm^{-1}$, which is similar to the acetate bound species, 2937 $cm^{-1}$.

Next, we evaluated the reactivity of Zn(HDMTH)($CO_3CH_3$) with hydride sources to assist with the reduction of $CO_2$ to $HCO_2^-$. The reaction of a chemical source of hydride, $NaBH_4$, with Zn(HDMTH)($CO_3CH_3$) was examined. In a typical experiment, the Zn(HDMTH)($CO_3CH_3$) complex was generated from the parent complex in methanol under constant bubbling of $CO_2$. An excess of $NaBH_4$ was added and the reaction stirred for 30 minutes. Analysis of the reaction mixture by $^1H$ NMR confirmed the formation of $HCO_2^-$ with 190 turnovers. Control experiments in the absence of Zn(DMTH)($CO_3CH_3$) were conducted yielding 62 turnovers for the uncatalyzed reaction. The results confirm Zn(DMTH)($CH_3OH$) is able to fix $CO_2$ from a gaseous stream and catalyze its reduction to $HCO_2^-$ with hydride.

To test if the reduction of $CO_2$ to $HCO_2^-$ can be achieved using electrochemical (e.g., electrocatalytic) hydride sources, controlled potential coulometry (CPC) was conducted using a platinum (Pt) working electrode. Pt electrodes catalyze the hydrogen evolution reaction (HER) via a Pt-hydride intermediate with no observed $CO_2$ reduction in the absence of a co-catalyst. A solution of Zn(HDMTH)($CO_3CH_3$) was prepared in methanol under constant bubbling of $CO_2$. A potential of −2.00 V vs. ferrocenium/ferrocene (Fc+/Fc) was applied for 24 hours during which 55.8 C of charge was consumed. Analysis of the reaction mixture by $^1H$ NMR confirmed the presence of $HCO_2^-$ with a total of 8.70 turnovers. The relatively low number of turnovers as compared the $NaBH_4$ study results from the fact that catalytic turnover in electrochemical reaction can occur in the diffusion layer, whereas the chemical reaction occurs throughout the bulk. The faradaic efficiency for $CO_2$ reduction based on the total charge is 30.1%. A substantial portion of the charge is associated with hydrogen evolution at Pt, which was found to account for 38.6 C in control experiments in the absence of our co-catalyst. Of the additional 17.2 C consumed upon addition Zn(DMTH)($CH_3OH$), 97.8% is associated with $HCO_2^-$ production.

Figure 5:
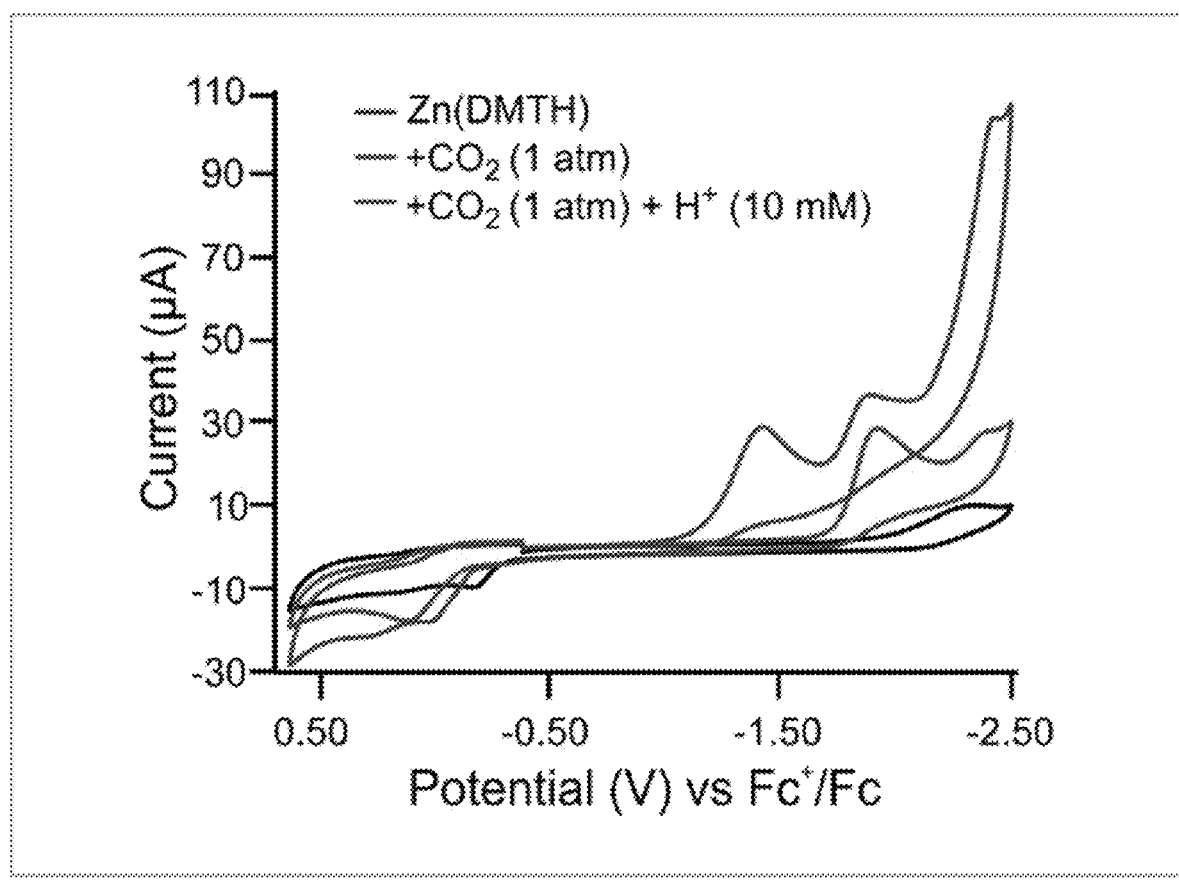
FIG. 5: Cyclic voltammograms of Zn(DMTH) recorded at a scan rate of 200 mV/s in 9:1 acetonitrile:methanol solution containing 0.1 M tetrabutylammonium hexafluorophosphate as supporting electrolyte with a glassy carbon working electrode, platinum counter electrode, and a Ag/AgCl reference electrode. Potentials are scaled to an internal $Fc^+/Fc$ standard. Traces shown are Zn(DMTH) (black), Zn(DMTH)+1 atm $CO_2$ (red), and Zn(DMTH)+1 atm $CO_2$ then +10 mM acetic acid (blue). All scans are from −0.48V to −2.5 V to 0.60 V to −0.48V and background corrected.

To determine if Zn(DMTH)($CH_3OH$) is able to catalyze $CO_2$ reduction in the absence of external hydride sources, CV experiments using a glassy carbon working electrode were performed. The CV of Zn(DMTH) in acetonitrile:methanol (9:1) at a scan rate of 200 mV/s shows an irreversible reduction ($E_{pc}$=−2.12 V vs. Fc+/Fc) and two irreversible oxidations ($E_{pa1}$=−0.27 and $E_{pa2}$=−0.13 V) (FIG. 5 black). Upon addition of $CO_2$, a new peak attributed to the reduction of Zn(HDMTH)($CO_3CH_3$) is observed at −1.87 V with a small catalytic peak at −2.37 V (FIG. 5 red). Addition of acetic acid results in an increase in the current of the catalytic peak at −2.37 V and an additional reduction event at −1.40 V (FIG. 5 blue). The peak at −1.40 V is attributed to the [Zn($H_2$DMTH)($CO_3CH_3$)]$^{+/0}$ couple resulting from the protonation of the hydrazonato nitrogen of the thiosemicarbazone group. This event is shifted by +470 mV relative to the [Zn(HDMTH)($CO_3CH_3$)]$^{0/-}$ couple at −1.87 V. It should be noted the presence of both peaks indicates an equilibrium between [Zn(HDMTH)($CO_3CH_3$)] and [Zn($H_2$DMTH)($CO_3CH_3$)]. The catalytic peak at −2.39 V is associated with the further reduction of Zn($H_2$DMTH)($CO_3CH_3$). Analysis of the catalytic peak under scan rate independent conditions with 10 mM acetic acid yield a turnover frequency (TOF) of 73.4 $s^{-1}$ with an overpotential of 0.86 V. Since Zn(DMTH) can sometimes adhere to glassy carbon under extended catalytic conditions, data were analyzed from CV traces on fresh electrode surfaces. Without being bound by theory, mechanistically, if acetic acid associates with Zn(DMTH) prior to $CO_2$, catalytic HER can be observed. This is attributed to protonation of the 2-pyridylhydrazonato N, which is the internal base for $CO_2$ fixation. Under turnover conditions, the insertion of $CO_2$ into Zn(DMTH)($CH_3OH$) appears to be kinetically preferred to protonation at acetic acid concentrations of 10 mM or less. At acetic acid concentrations above 10 mM in 9:1 acetonitrile:methanol catalytic HER can be observed at −3.29 V vs. Fc+/Fc. Attempts using phenol (96.8 mM-pKa=14.33) as a weaker acid showed no catalytic wave above background catalyst and $CO_2$.

To quantify the product of $CO_2$ reduction with Zn(DMTH) at a glassy carbon electrode, a series of CPC experiments were performed in the presence of acetic acid and slow bubbling of $CO_2$ for 24 hours (Table 1) at a potential of −2.30 V vs Fc+/Fc. The current remained constant over the course of the experiment with no sign of catalyst degradation. In all cases, including control experiments, $H_2$ was observed as a product in the headspace via gas chromatography. Analysis of the reaction solution via $^1H$ NMR revealed the production of formate or formic acid, depending on the reaction solvent, when Zn(DMTH) was present as a catalyst. No formate or formic acid was detected in control experiments in the absence of Zn(DMTH). The highest average charge and best average faradaic efficiencies were observed with Zn(DMTH) in 9:1 acetonitrile:methanol solution saturated with a stream of $CO_2$ at a glassy carbon electrode. Based on total charge consumed, these solutions yielded a faradaic efficiency of 29.2% for formic acid with a total of 16 turnovers. Notably, formic acid production accounts for 95.5% of the charge in excess of the background.

TABLE 1

Compilation of average faradaic efficiencies for the reduction of carbon dioxide to formate by Zn(DMTH) under various CPC conditions.[a]

| Working Electrode | Solvent | $CO_2$ Source[b] | Charge Consumed (C) | | Faradaic Efficiency (%) | |
| --- | --- | --- | --- | --- | --- | --- |
| | | | Total | Corrected[c] | Overall | Corrected.[d] |
| Pt | MeOH | 1 atm | 49.7-55.8 | 11.1-17.2 | 15.6-30.1 | 70.3-97.8 |
| GC | MeCN:MeOH | 1 atm | 102.7-101.1 | 29.4-31.4 | 27.7-29.2 | 93.9-95.6 |

TABLE 1-continued

Compilation of average faradaic efficiencies for the reduction of carbon dioxide to formate by Zn(DMTH) under various CPC conditions.[a]

| Working Electrode | Solvent | $CO_2$ Source[b] | Charge Consumed (C) | | Faradaic Efficiency (%) | |
|---|---|---|---|---|---|---|
| | | | Total | Corrected[c] | Overall | Corrected.[d] |
| GC | MeOH | 1 atm | 98.0-98.3 | 24.6-24.9 | 18.7-24.1 | 75.0-95.0 |
| GC | MeOH | Air | 51.9-63.3 | 15.7-27.1 | 14.3-15.8 | 36.9-47.6 |

[a]All experiments conducted for 24 hours;
CPC = controlled potential coulometry,
Pt = platinum electrode,
GC = glassy carbon electrode,
MeOH = methanol,
MeCN = acetonitrile (MeCN).
[b]1 atm $CO_2$ was obtained from a $CO_2$ cylinder (99.9%), gas was passed through a drying tube prior to introduction to the cell; $CO_2$ from air was obtained by using an air pump to introduce laboratory air into the solution with no pre-purification.
[c]The corrected charge is the total charge obtained in the presence of substrate and Zn(DMTH) minus the charge obtained under identical substrate conditions without Zn(DMTH).
[d]The overall faradaic efficiency is calculated based the quantity of formate produced relative to the total charge consumed; the corrected faradaic efficiency is calculated using the corrected charge.

Figure 6:
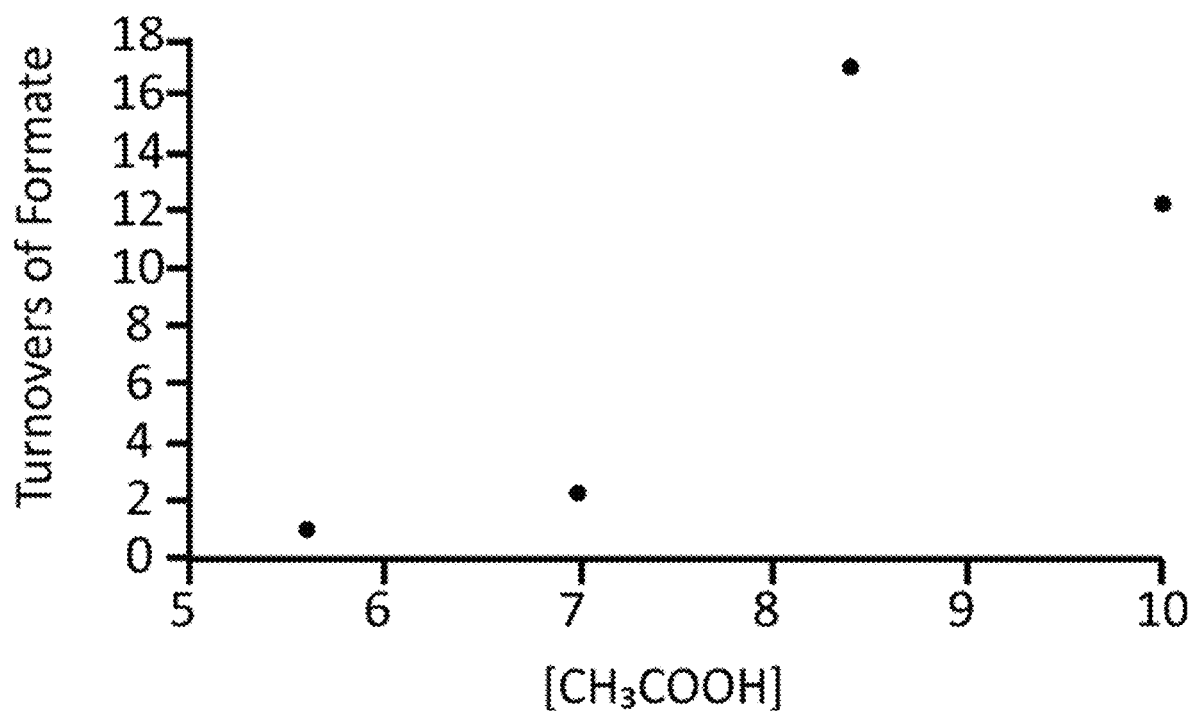
FIG. 6: Turnovers of formate as a function of acetic acid concentration with a glassy carbon electrode.

The subtraction of the background activity allows evaluation of the faradaic efficiency for the homogeneous catalyst. In methanol solution, Zn(DMTH) at a glassy carbon electrode provided a total of 12 turnovers with a faradaic efficiency of 24.1% based on total charge under a stream of $CO_2$. Acetic acid concentrations between 5.5 mM and 7 mM show low production of formate (between 1 and 3 turnovers of formate). Acetic acid concentrations at 8.3 and 10 mM acetic acid provided a higher number of formate turnovers (FIG. 6). To confirm that $HCO_2^-$ is derived from $CO_2$, isotopic labeling studies with $^{13}CO_2$ were conducted. The resulting experiment showed a doublet centered at 8.44 ppm (J=139 Hz) for $H^{13}CO_2^-$ and a singlet at 8.44 ppm for $H^{12}CO_2^-$. The singlet intensity for $H^{12}CO_2^-$ is attributed to $CO_2$ generated by oxidation of solvent at the anode. Remarkably, when the reaction was repeated using air pumped into solution from the surroundings in place of a $CO_2$ stream, reduction to $HCO_2^-$ was observed with a total of 4 turnovers. The optimal faradaic efficiency is 15.8% based on total charge consumed and 47.6% for background corrected charge.

In certain examples, Zn(DMTH) catalyzes the sequestration, activation, and reduction of $CO_2$ to $HCO_2^-$ on its own or in tandem with a hydride source. In some embodiments, modification of this hydride source from the catalyst to a supporting co-catalyst (Pt) can lower the overpotential of the reaction. In other embodiments, Zn(DMTH) can maintain its activity at low pressure in the presence of oxygen and water allowing for direct capture and reduction of $CO_2$ from air. Without being bound by theory, the activity of Zn(DMTH) may result from the inclusion of a FLP for $CO_2$ fixation in a redox-active ligand framework that facilitates $CO_2$ reduction at a non-redox active Zn(II).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner. Indeed, various modifications of the invention in addition to those described herein will become apparent to those skilled in the art from the foregoing description and the accompanying figures. Such modifications are intended to fall within the scope of the appended claims.

What is claimed is:

1. A method for producing formate from carbon dioxide comprising contacting carbon dioxide with a composition, where the composition comprises (a) a compound selected from Formula (I), salts, optical isomers, geometric isomers, salts of isomers, derivatives thereof, and solvent associated complexes thereof, (b) a solution solvent, and (c) an acid;

wherein

Formula (I) is

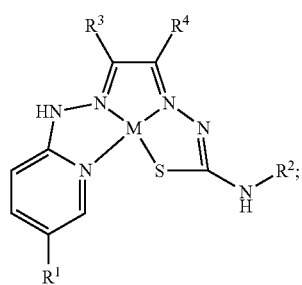

$R^1$ is monovalent H, halogen, —CN, nitro (—NO$_2$), —NH$_2$, —N(CH$_3$)$_2$, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which —NH$_2$, —N(CH$_3$)$_2$, methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

$R^2$ can be monovalent H, halogen, —CN, nitro (—NO$_2$), —NH$_2$, —N(CH$_3$)$_2$, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which —NH$_2$, —N(CH$_3$)$_2$, methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

$R^3$ can be monovalent H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy;

$R^4$ can be monovalent H, halogen, —CN, hydroxy (—OH), methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl, which methanoyl (—COH), carboxy (—CO$_2$H), C$_1$-C$_{10}$ alkyl, C$_2$-C$_{10}$ alkenyl, C$_2$-C$_{10}$ alkynyl, C$_1$-C$_9$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluorinated alkyl, —CF$_3$, —OCF$_3$, or C$_1$-C$_3$ alkoxy;

$R^3$ and $R^4$ are optionally bonded together to form a ring, where the ring that is formed can be cycloalkyl, heterocyclyl, aryl, or heteroaryl, which cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluorinated alkyl, —CF$_3$, —OCF$_3$, or C$_1$-C$_3$ alkoxy; and M is iron (Fe), nickel (Ni), palladium (Pd), cadmium (Cd), manganese (Mn), cobalt (Co), copper (Cu), gallium (Ga), or zinc (Zn).

2. The method of claim 1, wherein $R^1$ is monovalent H, halogen, —CN, nitro (—NO$_2$), —NH$_2$, —N(CH$_3$)$_2$, hydroxy (—OH), methanoyl (—COH), carboxy (—CO$_2$H), C$_1$-C$_7$ alkyl, C$_1$-C$_6$ alkoxy, cycloalkyl, heterocyclyl, aryl, or heteroaryl, which —NH$_2$, —N(CH$_3$)$_2$, methanoyl (—COH), carboxy (—CO$_2$H), C$_1$-C$_7$ alkyl, C$_1$-C$_6$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy.

3. The method of claim 1, wherein $R^1$ is H, Cl, Br, hydroxy (—OH), methanoyl (—COH), carboxy (—CO$_2$H), methyl, ethyl, n-propyl, or phenyl.

4. The method of claim 1, wherein $R^2$ is monovalent H, halogen, —CN, nitro (—NO$_2$), —NH$_2$, —N(CH$_3$)$_2$, hydroxy (—OH), methanoyl (—COH), carboxy (—CO$_2$H), C$_1$-C$_7$ alkyl, C$_1$-C$_6$ alkoxy, cycloalkyl, heterocyclyl, aryl, or heteroaryl, which —NH$_2$, —N(CH$_3$)$_2$, methanoyl (—COH), carboxy (—CO$_2$H), C$_1$-C$_7$ alkyl, C$_1$-C$_6$ alkoxy, cycloalkyl, heterocyclyl, aryl, or heteroaryl can optionally be substituted with one or more of halogen, oxo (=O), hydroxy (—OH), methanoyl (—COH), carboxy (—CO$_2$H), nitro (—NO$_2$), —NH$_2$, —N(CH$_3$)$_2$, cyano (—CN), ethynyl (—CCH), propynyl, sulfo (—SO$_3$H), morpholinyl, —CO-morpholin-4-yl, phenyl, —CONH$_2$, —CON(CH$_3$)$_2$, C$_1$-C$_3$ alkyl, C$_1$-C$_3$ perfluoronated alkyl, —CF$_3$, —OCF$_3$, or C$_1$-C$_3$ alkoxy.

5. The method of claim 1, wherein $R^2$ is H, Cl, Br, hydroxy (—OH), methanoyl (—COH), carboxy (—CO$_2$H), methyl, ethyl, n-propyl, or phenyl.

6. The method of claim 1, wherein $R^3$ is H, Cl, hydroxy (—OH), methyl, ethyl, C$_{1-5}$ alkyl, C$_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

7. The method of claim 1, wherein $R^3$ is H, methyl, ethyl, n-propyl, or phenyl.

8. The method of claim 1, wherein $R^4$ is H, Cl, hydroxy (—OH), methyl, ethyl, $C_{1-5}$ alkyl, $C_3$ alkyl, —CN, ethynyl, —CONH$_2$, —CON(CH$_3$)$_2$, 2-(morpholinyl)ethoxy, —CO-morpholin-4-yl, ethoxy, methoxy, 5-hydroxy pyridyl, indolyl, 1,2,3,4-tetrahydroisoquinolyl, 1,2-methylenedioxyphenyl, 2,3-methylenedioxyphenyl, furyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, methylenedioxyphenyl, perfluorinated methyl, or perfluorinated ethyl.

9. The method of claim 1, wherein $R^4$ is H, methyl, ethyl, n-propyl, or phenyl.

10. The method of claim 1, wherein $R^3$ and $R^4$ are bonded together to form cyclobutyl, cyclopentyl, cyclohexyl, chlorocyclohexyl, fluorocyclohexyl, methoxycyclohexyl, ethoxycyclohexyl, methylcyclohexyl, trifluoromethylcyclohexyl, cycloheptyl, cyclooctyl, pyrrolidinyl, pyrrolinyl, imidazolidinyl, pyrazolidinyl, piperidyl, piperazinyl, indolinyl, morpholinyl, 5-hydroxy pyridyl, indolyl, 1,2,3,4-tetrahydroisoquinolyl, furyl, 1,2-methylenedioxyphenyl, 2,3-methylenedioxyphenyl, 2-chlorophenyl, 3-chlorophenyl, 4-chlorophenyl, 2-fluorophenyl, 3-fluorophenyl, 4-fluorophenyl, 2-methoxyphenyl, 3-methoxyphenyl, 4-methoxyphenyl, 2-methylphenyl, 3-methylphenyl, 4-methylphenyl, 2-ethoxyphenyl, 3-ethoxyphenyl, 4-ethoxyphenyl, 2-trifluoromethyl phenyl, 3-trifluoromethyl phenyl, 4-trifluoromethyl phenyl, 2-trifluoromethoxy phenyl, 3-trifluoromethoxy phenyl, 4-trifluoromethoxy phenyl, 3,5-dimethoxyphenyl, 3,5-diethoxyphenyl, 3,5-dimethylphenyl, 3,5-diethylphenyl, 3,5-dihydroxyphenyl, 3,5-difluorophenyl, 3,5-dichlorophenyl, 3,5-bis-trifluoromethyl phenyl, phenyl, naphthyl, tolyl, xylyl, benzyl, pyridyl, 3-pyridyl, or methylenedioxyphenyl.

11. The method of claim 1, wherein $R^3$ and $R^4$ are not bonded together.

12. The method of claim 1, wherein M is cadmium (Cd), manganese (Mn), gallium (Ga), or zinc (Zn).

13. The method of claim 1, wherein M is zinc (Zn).

14. The method of claim 1, wherein the solution solvent is selected from CH$_3$CN, water, a $C_1$-$C_8$ alcohol, methanol, ethanol, propanol, butanol, n-butanol, pentanol, hexanol, or a combination thereof.

15. The method of claim 1, wherein the solution solvent is selected from CH$_3$CN, methanol, ethanol, propanol, n-butanol, pentanol, or a combination thereof.

16. The method of claim 1, wherein the acid has a pKa of no more than about 14.

17. The method of claim 1, wherein the acid is acetic acid, Et$_3$NHBF$_4$, piperidinium tetrafluoroborate, phosphoric acid, or a combination thereof.

18. The method of claim 1, wherein the acid is acetic acid.

19. The method of claim 1, wherein the composition further comprises a hydride source.

20. The method of claim 1, wherein the composition further comprises a hydride source and the hydride source is a chemical hydride source or an electrochemical hydride source.

21. The method of claim 1, wherein the composition further comprises a chemical hydride source and the chemical hydride source is a metal hydride, NaBH$_4$, or LiAlH$_4$.

22. The method of claim 1, wherein the composition further comprises an electrochemical hydride source and the electrochemical hydride source is a platinum (Pt) electrode, a palladium (Pd) electrode, or a glassy carbon electrode.

23. The method of claim 1, wherein the composition further comprises an electrode.

24. The method of claim 1, wherein the composition further comprises an electrode and the electrode is a platinum (Pt) electrode, a palladium (Pd) electrode, or a glassy carbon electrode.

25. The method of claim 1, wherein the temperature of the composition is from 0° C. to 99° C.

26. The method of claim 1, wherein the source of carbon dioxide is from air, from the waste gas of a powerplant, from the byproduct of a chemical reaction, from the byproduct of a catalytic reaction, or a combination thereof.

27. The method of claim 1, wherein the source of the carbon dioxide is from a gas and the concentration of carbon dioxide in the gas is from about 0.01% to about 90%.

28. A method for producing formate from carbon dioxide comprising
(1) contacting carbon dioxide with a first composition to provide a second composition, where the first composition comprises (a) a compound selected from Formula (I), salts, optical isomers, geometric isomers, salts of isomers, derivatives thereof according to claim 1, and solvent associated complexes thereof and (b) a solution solvent, and
(2) adding acid to the second composition to produce formate.

* * * * *